United States Patent
Eckhouse et al.

(10) Patent No.: US 9,084,587 B2
(45) Date of Patent: Jul. 21, 2015

(54) METHOD AND APPARATUS FOR PERSONAL SKIN TREATMENT

(75) Inventors: Shimon Eckhouse, Haifa (IL); Tuvia Dror Kutscher, Shoham (IL); Gilead Bar-Ilan, Ein-Ayala (IL)

(73) Assignee: SYNERON MEDICAL LTD, Yokneam (IL)

(*) Notice: Subject to any disclaimer, the term of this patent is extended or adjusted under 35 U.S.C. 154(b) by 82 days.

(21) Appl. No.: 13/487,747

(22) Filed: Jun. 4, 2012

(65) Prior Publication Data

US 2013/0144280 A1 Jun. 6, 2013

Related U.S. Application Data

(63) Continuation of application No. PCT/IL2010/001014, filed on Dec. 2, 2010.

(60) Provisional application No. 61/267,054, filed on Dec. 6, 2009, provisional application No. 61/316,974, filed on Mar. 24, 2010.

(51) Int. Cl.
*A61B 17/00* (2006.01)
*A45D 26/00* (2006.01)
(Continued)

(52) U.S. Cl.
CPC ............... *A61B 17/00* (2013.01); *A45D 26/00* (2013.01); *A61B 17/54* (2013.01); *A61B 18/14* (2013.01);
(Continued)

(58) Field of Classification Search
CPC ............ A61H 1/00; A61B 18/18; H01S 3/08; E05B 49/00
USPC .................... 601/15; 606/9; 372/92; 70/278.3
See application file for complete search history.

(56) References Cited

U.S. PATENT DOCUMENTS

| | | | |
|---|---|---|---|
| 1,430,354 | A | 9/1922 | Burdick |
| 2,183,726 | A | 2/1939 | Sommer et al. |

(Continued)

FOREIGN PATENT DOCUMENTS

| | | |
|---|---|---|
| CA | 2495005 A1 | 2/2004 |
| CN | 1078383 A | 11/1993 |

(Continued)

OTHER PUBLICATIONS

Acne Clearance, LHE Clinical Casebook, Radiancy: Lighting the Future of Skin Care, © 2002.

(Continued)

*Primary Examiner* — William Thomson
*Assistant Examiner* — Victor Shapiro
(74) *Attorney, Agent, or Firm* — Smith Risley Tempel Santos LLC; Gregory Scott Smith

(57) ABSTRACT

An apparatus enabling a casual user in a residential set-up to perform himself almost every skin treatment procedure by using a variety of modules that may be inserted into an infrastructure frame. The apparatus presents a docking station and an applicator. The applicator simultaneously receives only two types of skin treatment modules, these may be replaced after use for modules providing a different type of skin treatment. Such skin treatment modules like epilator, shaver, exfoliation or abrasive module, suction head, and massage head apply a mechanical action to the skin. Ultrasound module applies ultrasound waves to the skin. Intense pulsed light and RF apply electromagnetic radiation to the skin. A combination of these modules may be used to provide a variety of skin treatments such as hair removal, skin rejuvenation, skin exfoliation, acne treatment, circumference reduction, and other skin treatments.

11 Claims, 23 Drawing Sheets

(51) Int. Cl.
  *B26B 21/40* (2006.01)
  *A61B 17/54* (2006.01)
  *A61B 18/14* (2006.01)
  *A61B 18/20* (2006.01)
  *A45D 27/29* (2006.01)
  *A61B 19/00* (2006.01)

(52) U.S. Cl.
  CPC ............... *A61B 18/203* (2013.01); *B26B 21/40* (2013.01); *B26B 21/4056* (2013.01); *A45D 27/29* (2013.01); *A61B 19/44* (2013.01); *A61B 2017/00747* (2013.01)

(56) References Cited

U.S. PATENT DOCUMENTS

| | | | |
|---|---|---|---|
| 2,231,095 A | 2/1941 | Sommer et al. | |
| 2,824,308 A | 2/1958 | Duncan | |
| 3,088,205 A | 5/1963 | Ellis | |
| D196,532 S | 10/1963 | Facci | |
| 4,016,886 A | 4/1977 | Doss et al. | |
| 4,182,329 A | 1/1980 | Smit et al. | |
| D269,294 S | 6/1983 | Rakocy et al. | |
| D271,015 S | 10/1983 | Geraets | |
| D271,199 S | 11/1983 | Geraets | |
| 4,444,190 A | 4/1984 | Mutzhas | |
| D274,462 S | 6/1984 | Rakocy et al. | |
| 4,553,936 A | 11/1985 | Wang | |
| 4,686,986 A | 8/1987 | Fenyo et al. | |
| 4,753,958 A | 6/1988 | Weinstein et al. | |
| 4,784,135 A | 11/1988 | Blum et al. | |
| 4,867,682 A | 9/1989 | Hammesfahr et al. | |
| 4,869,584 A | 9/1989 | Dion | |
| 4,979,180 A * | 12/1990 | Muncheryan | 372/92 |
| 5,016,999 A | 5/1991 | Williams | |
| 5,169,384 A | 12/1992 | Bosrniak et al. | |
| 5,286,479 A | 2/1994 | Garlich et al. | |
| 5,316,473 A | 5/1994 | Hare | |
| 5,402,697 A | 4/1995 | Brooks | |
| 5,406,340 A | 4/1995 | Hoff | |
| 5,418,130 A | 5/1995 | Platz et al. | |
| 5,487,662 A | 1/1996 | Kipke et al. | |
| 5,521,392 A | 5/1996 | Kennedy et al. | |
| 5,582,476 A | 12/1996 | Hansen | |
| 5,611,793 A | 3/1997 | Wilson et al. | |
| 5,628,771 A | 5/1997 | Mizukawa et al. | |
| 5,642,997 A | 7/1997 | Gregg et al. | |
| 5,658,148 A | 8/1997 | Neuberger et al. | |
| 5,698,866 A | 12/1997 | Doiron et al. | |
| 5,704,935 A | 1/1998 | Pahl et al. | |
| 5,707,403 A | 1/1998 | Grove et al. | |
| 5,722,411 A | 3/1998 | Suzuki et al. | |
| 5,735,844 A | 4/1998 | Anderson et al. | |
| 5,755,753 A | 5/1998 | Knowlton | |
| 5,769,880 A | 6/1998 | Truckai et al. | |
| 5,814,008 A | 9/1998 | Chen et al. | |
| 5,824,023 A | 10/1998 | Anderson | |
| 5,836,999 A | 11/1998 | Eckhouse et al. | |
| 5,843,143 A | 12/1998 | Whitehurst | |
| 5,871,524 A | 2/1999 | Knowlton | |
| 5,919,219 A | 7/1999 | Knowlton | |
| 5,949,514 A | 9/1999 | Wargon | |
| 5,954,710 A | 9/1999 | Paolini et al. | |
| 5,961,543 A | 10/1999 | Waldmann | |
| 5,984,915 A | 11/1999 | Loeb et al. | |
| 5,993,180 A | 11/1999 | Westerhof et al. | |
| 6,056,548 A | 5/2000 | Neuberger et al. | |
| 6,063,108 A | 5/2000 | Salansky et al. | |
| 6,080,127 A | 6/2000 | Li et al. | |
| 6,080,391 A | 6/2000 | Tsuchiya et al. | |
| 6,081,934 A | 7/2000 | Stefanovsky et al. | |
| 6,107,326 A | 8/2000 | Jori | |
| 6,132,701 A | 10/2000 | Perez et al. | |
| 6,190,609 B1 | 2/2001 | Chapman et al. | |
| 6,191,110 B1 | 2/2001 | Jaynes et al. | |
| 6,210,402 B1 | 4/2001 | Olsen et al. | |
| 6,221,095 B1 | 4/2001 | Van Zuylen et al. | |
| 6,231,593 B1 | 5/2001 | Meserol | |
| 6,251,127 B1 | 6/2001 | Biel | |
| 6,258,319 B1 | 7/2001 | Hearst et al. | |
| 6,280,438 B1 * | 8/2001 | Eckhouse et al. | 606/9 |
| 6,288,498 B1 | 9/2001 | Cheng | |
| 6,308,413 B1 | 10/2001 | Westerhof et al. | |
| 6,343,400 B1 | 2/2002 | Massholder et al. | |
| 6,343,933 B1 | 2/2002 | Montgomery et al. | |
| 6,353,763 B1 | 3/2002 | George et al. | |
| 6,374,653 B1 * | 4/2002 | Gokcebay et al. | 70/278.3 |
| 6,406,157 B1 | 6/2002 | Audet | |
| 6,413,268 B1 | 7/2002 | Hartman | |
| 6,425,912 B1 | 7/2002 | Knowlton | |
| 6,433,343 B1 | 8/2002 | Cimino et al. | |
| 6,461,567 B1 | 10/2002 | Hearst et al. | |
| 6,462,070 B1 | 10/2002 | Hasan et al. | |
| 6,471,716 B1 | 10/2002 | Pecukonis | |
| 6,487,447 B1 | 11/2002 | Weimann et al. | |
| 6,493,940 B2 | 12/2002 | Westerhof et al. | |
| 6,494,900 B1 | 12/2002 | Salansky et al. | |
| 6,497,702 B1 | 12/2002 | Bernaz | |
| 6,508,813 B1 | 1/2003 | Altshuler | |
| 6,514,243 B1 | 2/2003 | Eckhouse et al. | |
| 6,517,532 B1 | 2/2003 | Altshuler et al. | |
| 6,533,775 B1 | 3/2003 | Rizoiu | |
| 6,558,653 B2 | 5/2003 | Andersen et al. | |
| 6,572,637 B1 | 6/2003 | Yamazaki et al. | |
| 6,594,905 B2 | 7/2003 | Furst et al. | |
| 6,602,245 B1 | 8/2003 | Thiberg | |
| 6,612,819 B1 | 9/2003 | Furst et al. | |
| 6,618,620 B1 | 9/2003 | Freundlich et al. | |
| 6,632,002 B1 | 10/2003 | Chubb et al. | |
| 6,637,877 B1 | 10/2003 | Hartley et al. | |
| 6,662,054 B2 | 12/2003 | Kreindel et al. | |
| 6,663,620 B2 | 12/2003 | Altshuler et al. | |
| 6,676,655 B2 | 1/2004 | McDaniel | |
| 6,702,808 B1 | 3/2004 | Kreindel | |
| D490,156 S | 5/2004 | Fischer et al. | |
| D490,526 S | 5/2004 | Jonsen | |
| 6,758,845 B1 | 7/2004 | Weckwerth et al. | |
| 6,761,729 B2 | 7/2004 | Babaev | |
| 6,770,069 B1 | 8/2004 | Hobart et al. | |
| 6,780,838 B2 | 8/2004 | Lipton et al. | |
| 6,795,728 B2 | 9/2004 | Chornenky et al. | |
| RE38,643 E | 11/2004 | Sugaya et al. | |
| 6,887,260 B1 | 5/2005 | McDaniel | |
| 6,889,090 B2 | 5/2005 | Kreindel | |
| 7,006,874 B2 | 2/2006 | Knowlton et al. | |
| 7,013,179 B2 | 3/2006 | Carter et al. | |
| 7,118,563 B2 * | 10/2006 | Weckwerth et al. | 606/9 |
| 7,153,298 B1 | 12/2006 | Cohen | |
| 7,234,239 B2 | 6/2007 | Saito et al. | |
| 7,266,414 B2 | 9/2007 | Cornelius et al. | |
| 7,275,819 B2 | 10/2007 | Bleau | |
| 7,824,394 B2 * | 11/2010 | Manstein | 606/9 |
| 7,963,985 B2 | 6/2011 | Minamoto et al. | |
| 8,135,475 B2 | 3/2012 | Kreindel et al. | |
| 8,157,807 B2 | 4/2012 | Ferren et al. | |
| 8,202,268 B1 | 6/2012 | Wells et al. | |
| 2002/0104543 A1 | 8/2002 | Hollander et al. | |
| 2002/0120256 A1 | 8/2002 | Furuno et al. | |
| 2002/0143373 A1 | 10/2002 | Courtnage et al. | |
| 2002/0183245 A1 | 12/2002 | Hasan et al. | |
| 2002/0190337 A1 | 12/2002 | House et al. | |
| 2002/0198575 A1 | 12/2002 | Sullivan | |
| 2003/0032950 A1 | 2/2003 | Altshuler et al. | |
| 2003/0097162 A1 | 5/2003 | Kreindel | |
| 2003/0109871 A1 | 6/2003 | Johnson et al. | |
| 2003/0135250 A1 | 7/2003 | Lauman et al. | |
| 2003/0139790 A1 | 7/2003 | Ingle et al. | |
| 2003/0195494 A1 | 10/2003 | Altshuler et al. | |
| 2003/0199946 A1 | 10/2003 | Gutwein | |
| 2004/0010250 A1 | 1/2004 | Manna et al. | |
| 2004/0010298 A1 | 1/2004 | Altshuler et al. | |
| 2004/0064167 A1 | 4/2004 | Berry et al. | |
| 2004/0133251 A1 | 7/2004 | Altshuler et al. | |
| 2004/0143308 A1 | 7/2004 | Lundahl et al. | |

(56) References Cited

U.S. PATENT DOCUMENTS

| | | |
|---|---|---|
| 2004/0147984 A1 | 7/2004 | Altshuler et al. |
| 2004/0167501 A1 | 8/2004 | Island et al. |
| 2004/0193234 A1 | 9/2004 | Butler |
| 2004/0260210 A1 | 12/2004 | Ella et al. |
| 2005/0015042 A1 | 1/2005 | Sun et al. |
| 2005/0043653 A1 | 2/2005 | Trimmer et al. |
| 2005/0049543 A1 | 3/2005 | Anderson et al. |
| 2005/0137654 A1 | 6/2005 | Hoenig et al. |
| 2005/0137655 A1 | 6/2005 | MacFarland et al. |
| 2005/0143793 A1 | 6/2005 | Korman et al. |
| 2005/0147137 A1 | 7/2005 | Slatkine |
| 2005/0177139 A1 | 8/2005 | Yamazaki et al. |
| 2006/0036300 A1 | 2/2006 | Kreindel |
| 2006/0058712 A1* | 3/2006 | Altshuler et al. ............ 601/15 |
| 2006/0095096 A1 | 5/2006 | DeBenedictis et al. |
| 2006/0149343 A1 | 7/2006 | Altshuler et al. |
| 2006/0200213 A1 | 9/2006 | McDaniel |
| 2006/0206173 A1 | 9/2006 | Gertner et al. |
| 2006/0212098 A1 | 9/2006 | Demetriou et al. |
| 2006/0224217 A1 | 10/2006 | Burgmann et al. |
| 2006/0231568 A1 | 10/2006 | Lynn et al. |
| 2006/0247741 A1 | 11/2006 | Hsu et al. |
| 2006/0259102 A1 | 11/2006 | Slatkine |
| 2007/0016117 A1 | 1/2007 | Sliwa et al. |
| 2007/0093798 A1 | 4/2007 | Debenedictis et al. |
| 2007/0106349 A1 | 5/2007 | Karni et al. |
| 2007/0129711 A1 | 6/2007 | Altshuler et al. |
| 2007/0142881 A1 | 6/2007 | Hennings |
| 2007/0191821 A1 | 8/2007 | Boxer Wachler |
| 2007/0197895 A1 | 8/2007 | Nycz et al. |
| 2007/0239143 A1 | 10/2007 | Altshuler et al. |
| 2007/0271714 A1 | 11/2007 | Adam et al. |
| 2008/0033411 A1 | 2/2008 | Manvel Artyom et al. |
| 2008/0071334 A1 | 3/2008 | Hoenig et al. |
| 2008/0123238 A1 | 5/2008 | Campos et al. |
| 2008/0215124 A1 | 9/2008 | Wagenaar et al. |
| 2008/0221504 A1 | 9/2008 | Aghion |
| 2008/0294153 A1 | 11/2008 | Altshuler et al. |
| 2008/0306476 A1 | 12/2008 | Hennings et al. |
| 2009/0036953 A1 | 2/2009 | Gustavsson |
| 2009/0043293 A1 | 2/2009 | Pankratov et al. |
| 2009/0112205 A1 | 4/2009 | McGill et al. |
| 2009/0182315 A1 | 7/2009 | Zigan et al. |
| 2009/0192503 A1 | 7/2009 | Epshtein et al. |
| 2009/0240310 A1 | 9/2009 | Kennedy |
| 2010/0063565 A1 | 3/2010 | Beerwerth et al. |
| 2010/0198134 A1 | 8/2010 | Eckhouse |
| 2010/0274329 A1 | 10/2010 | Bradley et al. |
| 2011/0137386 A1 | 6/2011 | Kreindel |
| 2011/0166559 A1 | 7/2011 | Eckhouse et al. |
| 2012/0143270 A1 | 6/2012 | Mehta |
| 2012/0290023 A1 | 11/2012 | Boyden et al. |
| 2013/0289679 A1 | 10/2013 | Eckhouse et al. |

FOREIGN PATENT DOCUMENTS

| | | |
|---|---|---|
| EP | 0743029 B1 | 7/2002 |
| EP | 0824019 B1 | 11/2002 |
| GB | 2125986 A | 8/1982 |
| GB | 2202442 A | 9/1988 |
| JP | 04299998 A2 | 10/1992 |
| JP | 06113920 A2 | 4/1994 |
| JP | 11132843 A2 | 12/1999 |
| JP | 2003034630 | 2/2003 |
| WO | WO-93/21992 A1 | 11/1993 |
| WO | WO-99/09143 A1 | 2/1999 |
| WO | WO-02/078644 A2 | 10/2002 |
| WO | WO-03/039367 A1 | 5/2003 |
| WO | WO-2006/128034 A1 | 11/2006 |
| WO | WO 2007137304 A2 * | 11/2007 |

OTHER PUBLICATIONS

Acne Star web page, describing "How to use get rid of Acne Treatment", printed May 5, 2005.

Acne Star web page, describing Clinical Studies, "The Treatment of acne vulgaris with a novel device that uses Gallium-Nitride diode light", printed May 5, 2005.

Aesthetic Buyers Guide: The Leading Cosmetic Practice Resource, Jan./Feb. 2004, vol. 7, No. I.

Bollen, CM. et al., "Full- versus partial-mouth disinfection in the treatment of periodontal infections. A pilot study: long-term microbiological observations". J Clin Periodontol Oct. 1996;23(10):960-70 (Abstract).

Bollen, CM. et al., "The effect of a one-stage full-mouth disinfection on different intra-oral niches. Clinical and microbiological observations", J Clin Periodontol Jan. 1998;25(1):56-66 (Abstract).

Calderi-Iead, R. Glen, "The Photobiology of LED Phototherapy".

Charakida et al., "Phototherapy in the Treatment of Acne Vulgaris, What is the Role'?", Am. J. Clin. Dermatol 2004; 5(4): 211-216.

Cohen LR., "What causes bad breath?", University of Toronto; webpage (printed before Nov. 2, 2004).

Coventry et al. (2000) "ABC of oral health: Periodontal disease" British Medical Journal, 321, 36-39.

De Soete, M. et al., "One-stage full-mouth disinfection. Long-term microbiological results analyzed by checker board DNA-DNA hybridization", J Periodontol Mar. 2001; 72(3):374-82 (Abstract).

Elman M. et al., "The effective treatment of acne vulgaris by a high-intensity, narrow bank 405-420 nm light source", Cosmetic & Laser Ther 2003; 5: 111-116.

Flow Control Network web page, "Mini Diaphragm Pumps for Precision Dispensing" by Ping Lin, printed Aug. 2, 2005.

Friedberg JS et al., "Antibody-Targeted Photolysis Bacteriocidal Effects of Sn (IV) Chlonn e6-Dextran-Monoclonal Antibody Conjugates", Annals New York Academy of Sciences 618:383-393, 1991.

Greenstein G., Full-mouth therapy versus individual quadrant root planning: a critical commentary, JPeriodontol Jul. 2002;73(7):797-812 (Abstract).

Hamblin, M. et al., "Rapid Control of Wound Infections by Targeted Photodynamic Therapy Monitored by In Vivo Bioluminescence Imagining", Photochemistry and Photobiology, 2002, 75(1): 51-57.

Komerik et al. (2003) "In vivo killing of *Porphyromonas gingivalis* by toluidine blue-mediated photosensitization in an animal model" Antimicrobial Agents and Chemotherapy, 47(3), 932-940.

Krespi, et al. (2005) "Lethal photosensitization of oral pathogens via red-filtered halogen lamp" Oral Diseases, 11(S1), 92-95.

Malik, Z. et al., "New Trends in Photobiology (Invited Review) Bactericidal Effects of Photoactivated Porphyrins—An Alternative Approach to Antimicrobial Drugs", Journal of Photochemistry and Photobiology, B: Biology, 5 _1_1990} _281-293.

Matevski D. et al., "Lethal photosensitization of periodontal pathogens by a red-filtered Xenon lamp in invitro", JPeriodont. Res. 2003. 38:428-435.

Matevski D. et al., "Sensitivity of *Porphyromonas gingivalis* to Light-Activated Toluidine Blue O", University of Toronto, Faculty of Dentistry; Slide presentation (presented before Nov. 15, 2002).

Meisel etal. (2005) "Photodynamic therapy for periodontal diseases: State of the are" J. Photochem. Photobiol., 79, 159-170.

Mongardini, C. et al., "One stage full- versus partial-mouth disinfection in the treatment of chronic adult or generalized early-onset periodontitis. I. Long-term clinical observations", J Periodontol Jun. 1999;70(6):632-45 1Abstrac!2._.

Morton C.A. et al., An open study to determine the efficacy of blue light in the treatment of mild to moderate acne: preliminary data (publication status unknown).

Nakano et al. (2002) "Correlation between oral malodor and periodontal bacteria" Microbes Infect., 4(6), 679-683.

Ondine Biopharma web page—printed Oct. 15, 2002.

Papageorgiou ct al., "Phototherapy with blue (415 nm) and red (660 nm) light in the treatment of acne vulgaris", British Journal of Dermatology 2000: 142: 973-978.

Pharmaceutical description, Levulan® Kerastick *arninolevulinic acid I-IC!) for Topical Solution, 20'X.

Quirynen, M. et al. "Full- vs. partial-mouth disinfection in the treatment of periodontal infections: short-term clinical and microbiological observations", J Dent Res Aug. 1995;74(8):1459-67 (Abstract).

(56) References Cited

OTHER PUBLICATIONS

Quirynen, M. et al., "The effect of a 1-stage full-mouth disinfection on oral malodor and microbial colonization of the tongue in periodontitis. A pilot study", J Periodontol Mar. 1998;69(3):374-82 (Abstract).

Quirynen, M. et al., "The intra-oral translocation of periodontopathogens jeopardises the outcome of periodontal therapy", Journal of Clincial Periodontology, Jun. 2001, vol. 28, Issue 6, p. 499 (Abstract).

Quirynen, M. et al., "The role of chlorhexidine in the one-stage full-mouth disinfection treatment of patients with advanced adult periodontitis. Long-term clinical and microbiological observations", J Clin Periodontol 2000 A1!JL2~579-89 J__Abstrac__!).

Quirynen. M. et al., "One stage full- versus partial-mouth disinfection in the treatment of chronic adult or generalized early-onset periodontitis. II. Long-term impact on microbial load", J Periodontol Jun. 1999;70(6):646-56 J Abstrac!2__.

Sanz et al. (2001) "Fundamentals of breath malodour" Journal of Contemporary Dental Practice, 2(4), 1-13.

Sarkar et al. (1993) "Lethal photosensitization of bacteria in subgingival plaque from patients with chronic periodontitis" J. Periodont. Res , 28, 204-21 O.

Skin91 I .corn web page regarding Peter Thomas Roth Clinical Acne Medication, acne treatrnent—Benzoyl Peroxide 5% pbp5, printed Apr. 19, 2005.

Soukos et al. (1998) "Targeted antimicrobial photochemotherapy", Antimicrobial Agents and Chemotherapy 42( 10 ), 2595-2601.

Spire Awarded Contract for Ear Surgery Laser—Press Release Aug. 23, 2002.

Temperatures.corn web page, "Thermistor Temperature Sensors," printed Aug. 2, 200.

Vandekerckhove, BN. et al.. "Full- versus partial-mouth disinfection in the treatment of periodontal infections. Long-term clinical observations of a pilot study", J Periodontol Dec. 1996;67(12):1251-9 (Abstract).

Wainwright M., Photodynamic antimicrobial chemotherapy (PACT), Journal of Antimicrobial Chemotherapy (1998) 42, 13-28.

Wilson (2005) "Lethal photosensitisation of oral bacteria and its potential application in the photodynamic therapy of oral infection" Photochem. Photobiol. Sci., 3, 412-418.

Wilson et al. (1995) "Bacteria in supragingival plaque samples can be killed by low-power laser light in the presence of a photosensitizer" J. Appl. Bacteriol., 78, 569-574.

Wood, et al. (1999) "An in vitro study of the use of photodynamic therapy for the treatment of natural oral plaque biofilrns formed in vivo" J. Photochem. Photogiol. B: Biol., 50, 1-7.

www.lightbioscience.com web page, Gentle Waves Cosmcceuticals, printed Jul. 29, 200.

www.lightbioscience.com web page, Gentle Waves LED Photomodulation Fact Sheet, printed Jul. 29, 2005.

PCT/IL10/00751 International Search Report.
PCT/IL10/01014 International Search Report.
PCT/IL11/00170 International Search Report.
PCT/IL11/00256 International Search Report.
PCT/IL11/00781 International Search Report.

* cited by examiner

VIEW E

VIEW G

DETAIL I-I.

SECTION D-D

METHOD AND APPARATUS FOR PERSONAL SKIN TREATMENT

CROSS-REFERENCE TO RELATED APPLICATIONS

This application is being filed under 37 U.S.C. 111 as a continuation application of International Application Number PCT/IL2010/001014, which has an international filing date of Dec. 2, 2010 and which claims priority to the following United States provisional applications for patent: Ser. No. 61/267,054 filed on Dec. 6, 2009 and 61/316,974 filed on Mar. 24, 2010. This application claims the benefit of the priority date Dec. 6, 2009 under 37 U.S.C. 120 as a continuation of PCT/IL2010/001014 which claims priority as previously stated. The International Application Number PCT/IL2010/001014 is co-pending at the filing of this application and includes at least one common inventor. This application incorporates the above-identified applications by reference in their entirety.

TECHNOLOGY FIELD

The method and apparatus disclosed herein are related to the field of personal cosmetic procedures and in particular to hair removal, wrinkle removal, acne removal, skin tightening, and other cosmetic procedures.

BACKGROUND

External appearance is important to practically every person. In recent years, methods and apparatuses have been developed for different cosmetic and dermatological treatments. Among these are hair removal, treatment of vascular lesions, wrinkle removal, skin rejuvenation and others. In some of these treatments, the skin and tissue are treated by one or more types of electromagnetic radiation such as radio frequency (RF) and optical radiation or illumination. When applied to the skin RF typically heats the skin. The illumination may be monochromatic (laser) or polychromatic including a narrow or broad spectrum of different wavelengths. The optical radiation depending on the wavelength may heat the skin, coagulate wounds, and produce photo-chemical effects. The time and intensity of the electromagnetic radiation are selected to achieve a desired effect, which is typically achieved by heating the treated skin segment to a temperature of 38-60 degrees Celsius.

The optical radiation is applied to the skin with the help of an applicator having an aperture of a given dimension. In order to "cover" the entire skin surface, the aperture has to be moved from place to place, in a relatively accurate fashion on a step equal to at least one aperture dimension, so that no areas of the skin will be missed or treated twice. In order to avoid this, the individual visually tracks applicator location. The optical radiation is frequently applied in a pulse mode. The light pulses inevitably reach his/her eyes, disturb the individual, and affect the applicator location tracking and skin treatment process. Applying optical radiation devices achieve the desired effect only if a certain energy density is applied to the skin and/or tissue. If the device is moved too quickly or too slowly across the skin, the device may be less efficacious or cause burns, respectively.

Optical radiation treats the upper skin layer and penetrates to a relatively shallow depth of no more than few millimeters. Radio Frequency (RF) is applied to the skin with the help of a pair or more electrodes that have to be in contact with the skin. RF voltage is applied across the electrodes in pulse or continuous waveform (CW). The properties of the RF voltage are selected to generate RF induced current in a volume or layer of tissue to be treated. This current heats the tissue to the required temperature, which is typically in the range of 38-60 degrees Celsius. For example, the temperature may destroy or injure the hair follicle or root and delay further hair growth, destroy or cause regeneration of the collagen tightening the skin over the treated skin segment. The effect may also be weakening of the hair shaft or even hair follicle or root destruction, collagen structure changes or destruction, and other.

Frequently the skin treatment by electromagnetic radiation is combined with mechanical procedures such as skin massages, mechanical hair removal, skin abrasion, ultrasound adipose tissue treatment, and other. For example, such desired effect as hair re-growth retardation, is typically achieved by illumination of an earlier mechanically depilated skin surface by laser, LED, Xenon lamp, Intense Pulsed Light (IPL), or incandescent lamp radiation, generally termed illumination or optical radiation. Circumference reduction is typically obtained by application of ultrasound or RF energy. Massage is known to stimulate blood flow and is frequently used for cosmetic procedures in combination with RF or illumination energy Professional equipment that combines light and RF treatment, massage and RF treatment also exists. Usually this equipment is configured to illuminate a defined segment of a subject skin generally similar or equal to the surface of the aperture through which optical radiation is directed to the skin segment. The electrodes are typically located proximal to the periphery of the aperture and the RF typically may heat deeper tissue layers than those heated by light thus destroying/injuring hair bulbs and/or hair follicles. There is a delicate relation between the amount of RF energy and optical radiation applied to the same skin segment. Exceeding the optimal proportion between them leads to skin burns, whereas application of lower than optimal proportion RF energy and optical radiation does not bring the desired treatment results.

The above-described equipment enabling mechanical hair removal, RF energy application, optical radiation treatment, ultrasound treatment, and other cosmetic treatments is both costly and bulky. Further, such equipment is typically operated in an ambulatory set-up by a qualified operator and frequently requires the presence of medical personnel specialized in such treatments. Certain skin treatment procedures may be performed by a user himself using the available on the market equipment enabling him/her to conduct typically one type of skin treatment only. The user however, does not get results similar or identical to those provided by professional equipment used for skin treatments, has no ability to perform all of the desired procedures, is not experienced in selecting proper treatment parameters and other equipment operational issues.

GLOSSARY

Several terms are utilized throughout this disclosure. The definition for these terms is provided here for convenience.

The term "illumination sources," "optical radiation sources," and "light sources" as used in the present disclosure has the same meaning and includes sources of visible and invisible infrared radiation.

As used herein, the term "skin treatment" may include such cosmetic procedures like complete or partial hair removal, hair growth retardation, skin rejuvenation, wrinkle reduction, waist tightening, vascular lesion removal, texture improvement, cellulite reduction, skin abrasion, acne effects reduction, etc.

The term "skin surface" relates to the most external skin layer, which may be stratum corneum.

The term "tissue" relates to skin layers located below the stratum corneum. The layers may be located immediately below the stratum corneum and as deep as 6 or even 7 mm below the stratum corneum.

As used herein, the term "hair removal" may include mechanical hair removal and hair growth retardation.

Titanium Dioxide ($TiO_2$) is a widely used white pigment in the plastic and coatings industry. $TiO_2$ efficiently scatters light.

Dermabrasion is a cosmetic procedure in which the surface of the skin and in particular the stratum corneum is removed by abrasion. The instrument used to perform the procedure is called a dermabrader.

The term "keyed connector" used throughout the document means a connector operative to provide power or receive signals from the powered device or module as well as optional module orientation and identification means.

BRIEF SUMMARY

A skin treatment apparatus for personal use for cosmetic skin treatment. The apparatus enables a user of providing different cosmetic procedures such as complete or partial hair removal and hair growth deterrent, wrinkle removal or skin smoothing, skin rejuvenation, skin massaging, and other procedures. The embodiments may include combinations of various interchangeable modules or elements that may include, but are not limited or required in all embodiments and in conducting different skin treatment procedures. Some of the modules enable application to the skin of (a) mechanical energy and processes for cutting, plucking or shaving hair follicles; massaging the skin for cellulite reduction and circumference changes; and skin abrasion or micro-abrasion for skin rejuvenation and acne removal; (b) modules enabling high frequency ultrasound to skin applications (c) modules and/or cartridges to provide the application of electromagnetic energy in form of skin illumination by different wavelengths or RF energy heating the skin; (d) further skin treatment techniques including the application of solutions before, after and/or during the mechanical process and/or the application of heat and/or energy. Each of the listed above processes may be applied alone or in combination with other processes or in different application sequences.

In order to conduct the desired cosmetic skin treatment the user applies applicator to the skin and couples to it one or more types of energy. The user displaces the applicator along the skin treating different skin segments. An optional displacement speed monitoring arrangement monitors the displacement speed and establishes the optical power as a function of the device displacement speed. Other sensors such as movement direction sensors, accelerometers, impedance sensors, as well as module identification tags may affect treatment parameters. Overall, the various embodiments operate to treat an area of skin, to facilitate the removal of all or a portion of hair, retard further growth, wrinkle removal or skin smoothing, acne reduction, adipose tissue distraction, and rejuvenation or health maintenance of the skin surface.

BRIEF DESCRIPTION OF THE SEVERAL VIEWS OF THE DRAWING

The disclosure is provided by way of non-limiting examples only, with reference to the accompanying drawings, in which like reference characters refer to the same parts throughout the different views. The drawings are not necessarily to scale, emphasis instead being placed upon illustrating the principles of the method.

DETAILED DESCRIPTION OF EXEMPLARY EMBODIMENTS

The principles and execution of the apparatus and the method described thereby may be understood with reference to the drawings and the accompanying description of non-limiting, exemplary embodiments.

Figure 1:
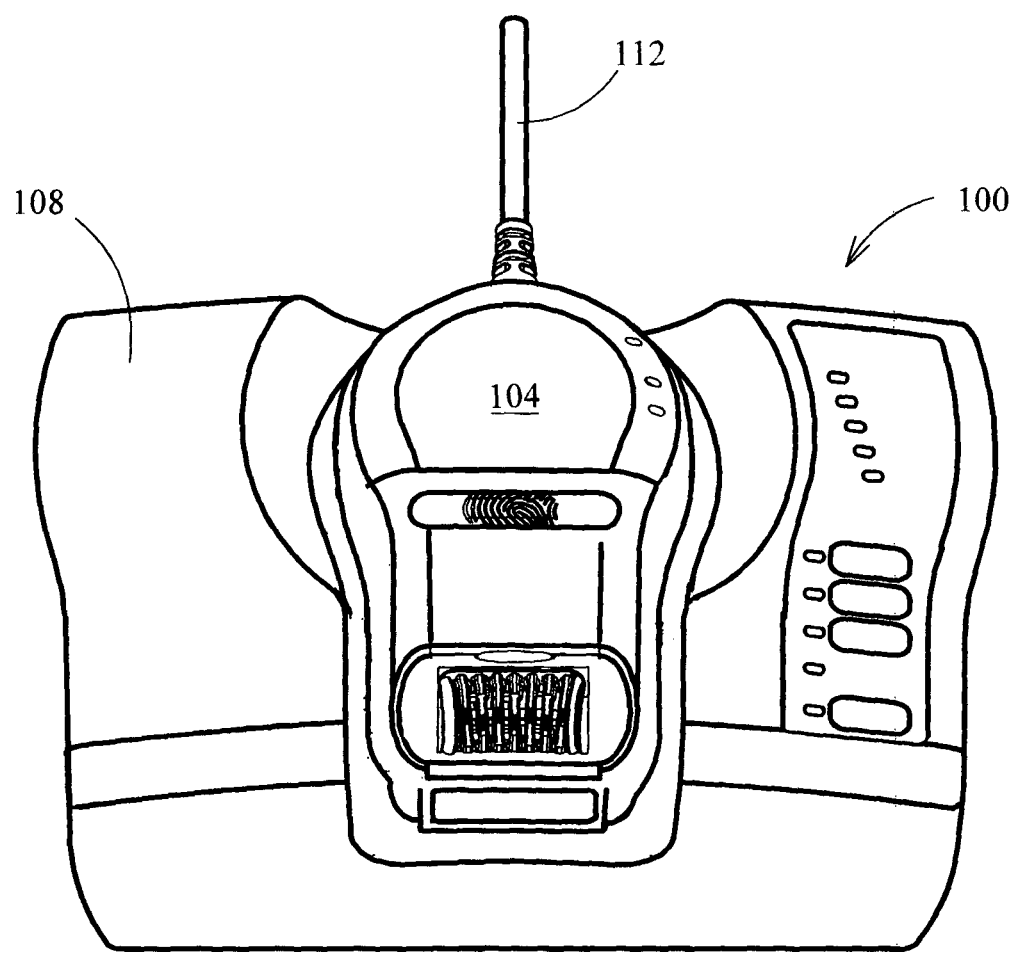
FIG. 1 is a schematic illustration of an exemplary embodiment of the apparatus for personal use for skin treatment.

Reference is made to FIG. 1, which is a schematic illustration of an exemplary embodiment of the apparatus for personal use for skin treatment. Apparatus 100 comprises an applicator or device 104 adapted for sliding movement on a subject skin, a docking unit 108, and a cord 112 (shown partially) connecting between applicator 104 and docking unit 108. Cord 112 enables electric and fluid communication between applicator 104 and docking unit 108. Apparatus 100 may receive power supply from a regular electric supply network receptacle. Applicator 104 may receive power supply from a rechargeable or regular battery. Docking unit 108 would typically charge the rechargeable batteries of applicator 104.

Figure 2:
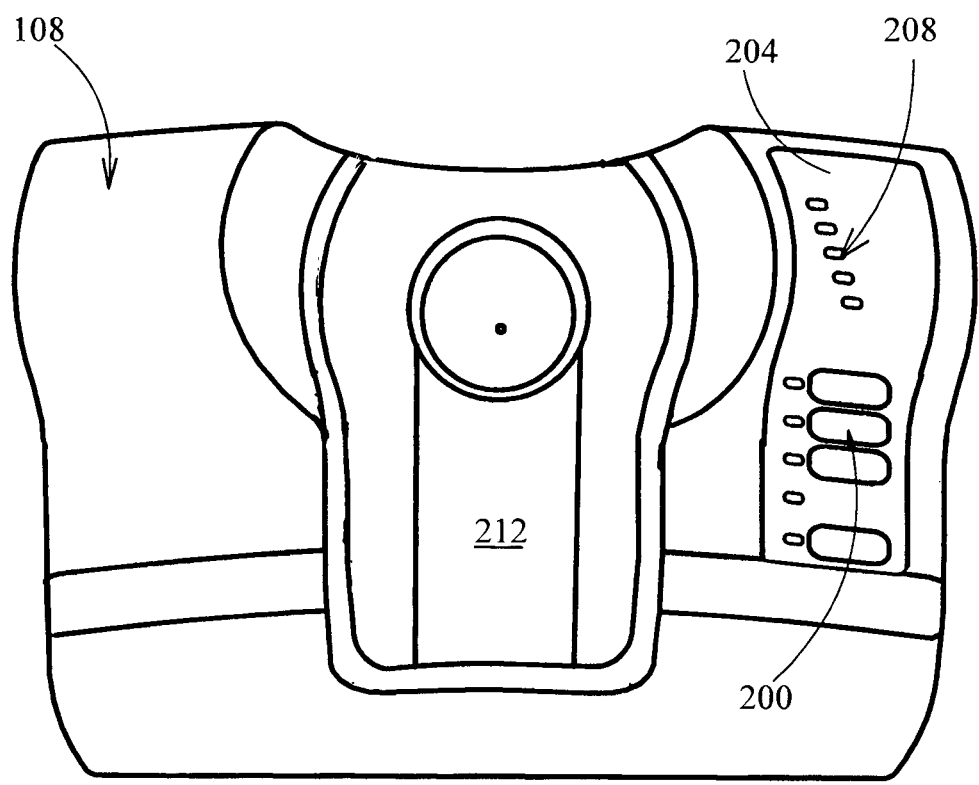
FIG. 2 is a schematic illustration of an exemplary embodiment of the docking unit of the apparatus for personal use for skin treatment.

FIG. 2 is a schematic illustration of an exemplary embodiment of the docking unit of the apparatus for personal use for skin treatment. Docking unit 108 includes a number of push buttons 200 located on panel 204 and enabling the user to operate apparatus 100 (FIG. 1), a number of operational status indicators 208 informing the operator on the status of different procedures performed with the help of the apparatus 100, and a docking bay 212 receiving applicator 104. A receptacle (not shown) facilitates connection of the docking unit to a regular electric supply network. Push buttons 200 may have built-in LEDs or other light sources and serve as additional process status indicators.

Figure 3:
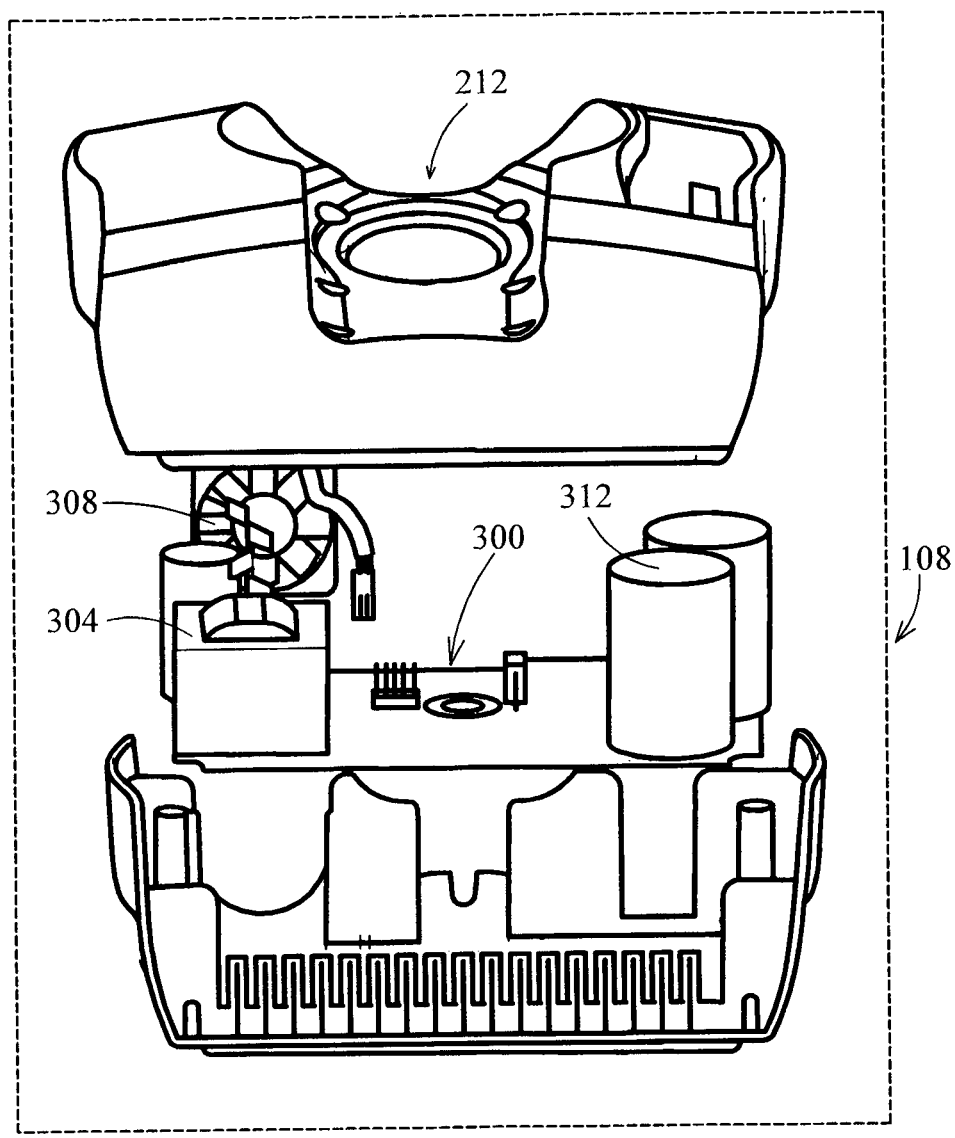
FIG. 3 is a schematic illustration of an exploded assembly of the docking unit of the apparatus for personal use for skin treatment.

FIG. 3 is a schematic illustration of an exploded assembly of the docking unit of the apparatus for personal use for skin treatment. Docking unit 108 houses a control board 300, a power supply 304, where the power supply may include a transformer with or without current rectifier, a cooling fan 308, vacuum pump 312, and other auxiliary units that may provide additional functionality beneficial to the selected skin treatment. Control board 300 controls almost all functions of the apparatus 100 (FIG. 1) and communicates with a control board 708 (FIG. 7) of applicator 104. Power supply 304 provides the necessary for operation of different skin treatment modules electric power.

Figure 4:
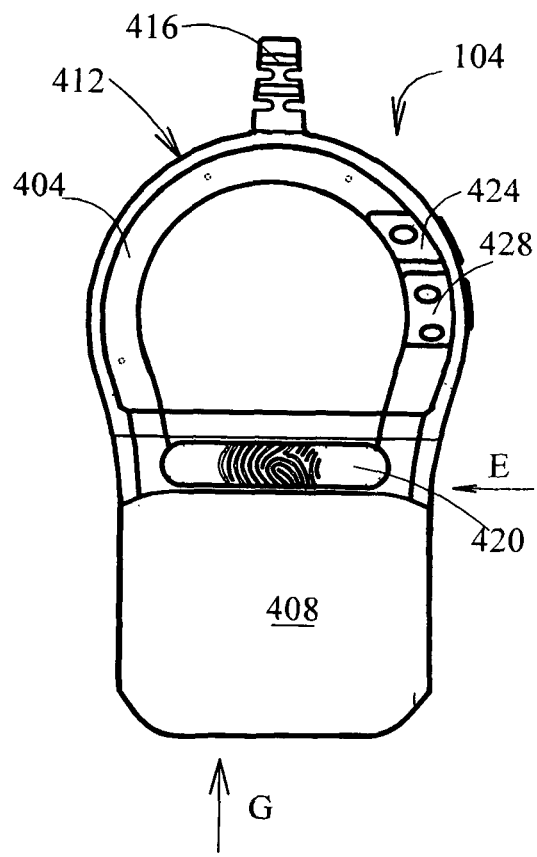
FIG. 4 is a schematic illustration of a frontal view of an exemplary embodiment of the applicator of the apparatus for personal use for skin treatment.

FIG. 4 is a schematic illustration of a frontal view of an exemplary embodiment of the applicator of the apparatus for personal use for skin treatment. Applicator 104 is shown to include an ergonomically designed casing 404 which fits the hand palm, having a first or distal end at which infrastructure frame 408 is located and a second end 412. The second end 412 includes a receptacle 416 enabling connection of applicator 104 with help of cord 112 (FIG. 1) to docking unit 108. Also shown in the Figure are a grip sensor 420 located on both sides (FIGS. 4 and 5) of applicator 104, an ON/OFF indicator 424 informing the user of the operational status of the illumination module 1500 (FIG. 15) of the applicator and indicator 428 informing the user on type of the skin (fair or dark) treatment module inserted in the applicator 104 and their operational status. It may also inform him of the type of treatment for which the cartridge is indicated (For example hair removal, skin rejuvenation, acne treatment, and etc.). It should be emphasized that the concept can also work with no indication at all from the module as to the type of treatment. The module will operate according to the type of treatment of for which the cartridge was dedicated and the settings made on the base (high, medium, or low power) will change automatically according to the cartridge inserted in a way completely transparent to the user. (The apparatus will detect automatically the type of the cartridge.). The indicators depending on their state may light with the same or different color and a combination of indicators and their colors may indicated on presence and operation of a particular skin treatment module. Grip sensor 420 serves as a safety feature. When a user holds applicator 104 he or she naturally presses grip sensor 420 and enables different voltage supplies to different functional modules inserted into infrastructure frame 408. The first end of applicator 104 features two receiving bays shown in FIGS. 5 and 6 accepting different cosmetic skin treatment modules.

Figure 5:
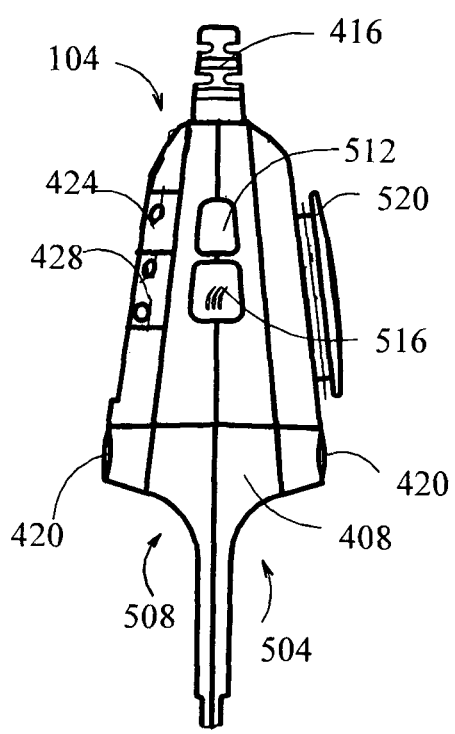
FIG. 5 is a schematic illustration of a side view of an exemplary embodiment of the applicator of the apparatus for personal use for skin treatment.

FIG. 5 is a schematic illustration of a side view in the direction of arrow E of an exemplary embodiment of the applicator of the apparatus for personal use for skin treatment. The distal or first end 408 of applicator 104 includes two receiving bays 504 and 508 operative to receive at least one of a group of modules for performing cosmetic skin treatment. As it will be explained in detail below, these may be a module for hair shaving, a module for hair depilation or epilator module, a module for skin illumination, a skin abrading module, a skin massaging module, and other modules. For safety reasons electric contacts of each of the modules may be configured to activate electricity supply to the module only when the module is inserted into the appropriate location. Push button 512 is an ON/OFF switch that activates or switches off one of the modules for skin illumination 1500 (FIG. 15) when such is inserted in the appropriate receiving bay. Push button 516 activates other modules. In addition to this a number of pushes on the button 516 may enable setting different operating parameters for each of the modules. A decorative cover 520 covers an air intake opening of the applicator 104.

Figure 6:
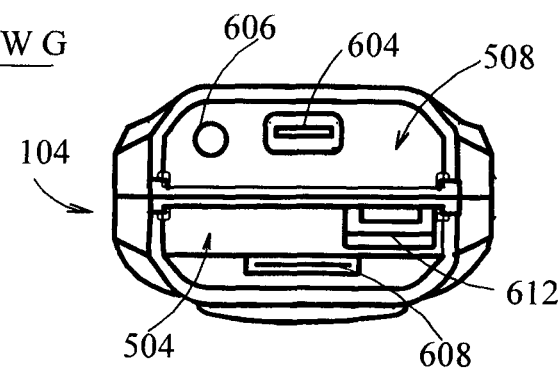
FIG. 6 is a schematic illustration of a bottom view of an exemplary embodiment of the applicator of the apparatus for personal use for skin treatment.

FIG. 6 is a schematic illustration of a bottom view in the direction of arrow G of the exemplary embodiment of the applicator of the apparatus for personal use for skin treatment. Receiving bay 508 is operative to receive and provide a mechanical and electrical interface to any one of the skin treatment modules having an identical interface. Such modules may be a module for hair shaving, a module for hair depilation, acne RF and vacuum treatment module, a module for skin rejuvenation, a skin massage module, and other. Connector 604 has a type of key mechanism preventing insertion of a non-matching type of module and opening 606 serves for connection to vacuum pump 312 (FIG. 3). Receiving bay 508 is operative to receive and provide a mechanical and electrical interface to any one of the illumination modules. Such modules may be a module that includes an incandescent lamp, a module with xenon lamp or Xenon IPL lamp, a module with laser diode, LED, or a combination of two or more of illumination sources or other modules with matching interface. Connector 608 also has a type of key mechanism preventing insertion of a non-matching type of module. In addition each of the skin treatment modules includes a tag identifying the module and setting the module operational parameters. The tag may be an RFID, EEPROM, or a simple electronic circuit with unique characteristics such as resistance, capacitance, and others. Opening 612 provides an input channel to a flow of cooling fluid, which may be a gas or simply air.

Figure 7:
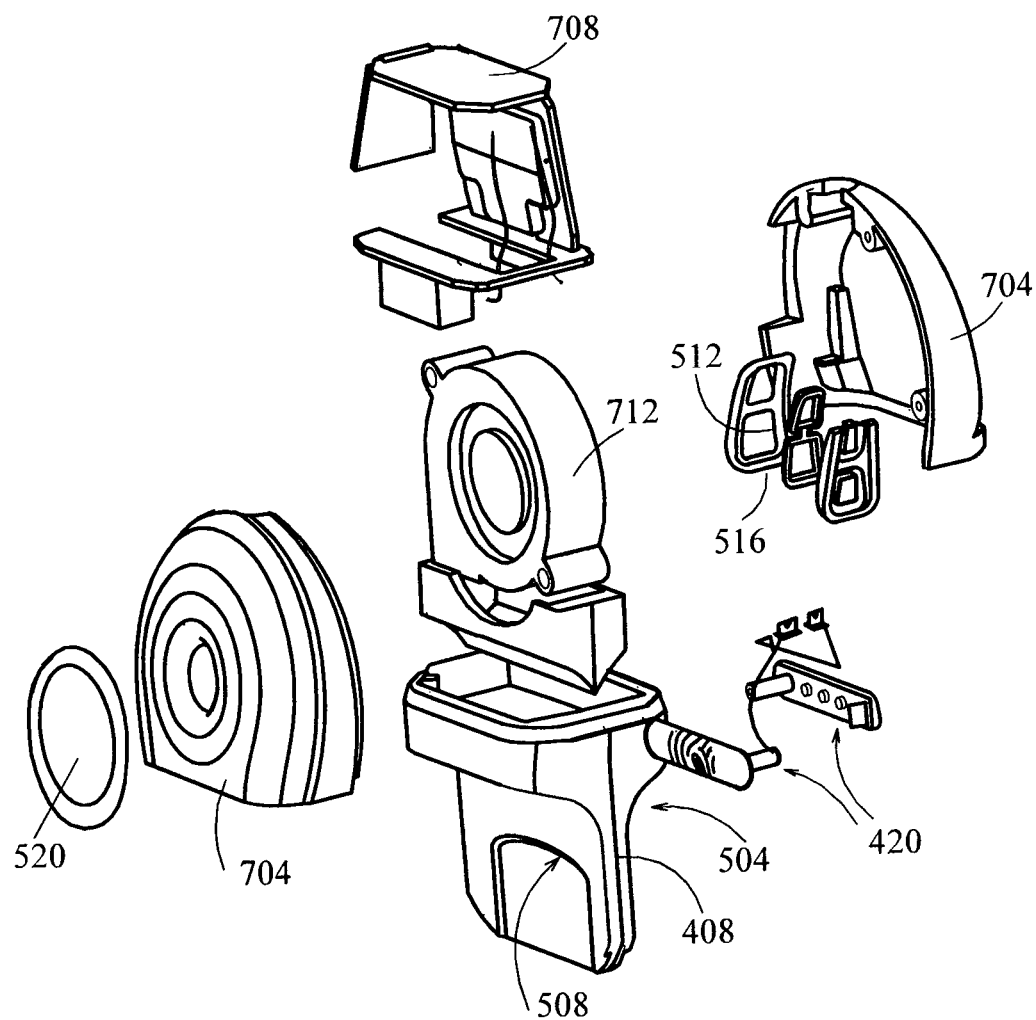
FIG. 7 is a schematic illustration of an exploded assembly of the applicator of the apparatus for personal use for skin treatment.

FIG. 7 is a schematic illustration of an exploded assembly of the applicator of the apparatus for personal use for skin treatment. Applicator 104 includes a two part case 704 incorporating a control printed circuit board 708 which for packaging purposes is divided into a number of electrically communicating segments, a blower or a fan 712 providing a stream of cooling fluid to the illumination module (not shown), and grip sensors 420. According to some embodiments of the disclosure, the blower 712 is rotary blower that blows air shown by arrows 1828 (FIG. 18) into one side of the illumination or optical radiation providing module, cools the disposable cartridge 1800, the source of optical radiation 1808 and the reflector 1812 and emerges from the opposite side as shown by arrows 1828 of the optical radiation providing module. Control circuit board 708 may include different sensors such as movement direction sensors, accelerometers, impedance sensors, and others as well as control circuitry of micro switches operated by insertion of different module, temperature sensors processing circuits, module tag identification and treatment parameters setting circuit, and others. Alternatively, some of the sensors may be located in appropriate skin treatment modules and their processing circuits may be located on control board 308 (FIG. 3) At least one optional audio status indicator such as a buzzer signaling to the user the status of skin treatment process parameters may be attached to applicator 104. Alternatively, a buzzer may be located in base unit 108.

Figure 8:
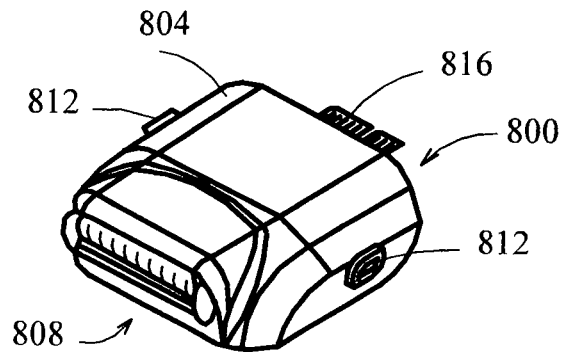
FIG. 8 is a schematic illustration of a perspective view of an exemplary embodiment of a hair shaving module of the apparatus for personal skin treatment.

FIG. 8 is a schematic illustration of a perspective view of an exemplary embodiment of a shaver module of the apparatus for personal skin treatment. Shaver module 800 includes a case 804 incorporating a hair shaving or hair removal mechanism 808 to be disclosed in detail below, a pair of release buttons 812 enabling easy shaver module release from the applicator, a keyed connector 816, and a tag identifying the module and setting the module operational parameters. The tag may be an RFID, EEPROM, or a simple electronic circuit with unique characteristics such as resistance, capacitance, and others.

Figure 9:
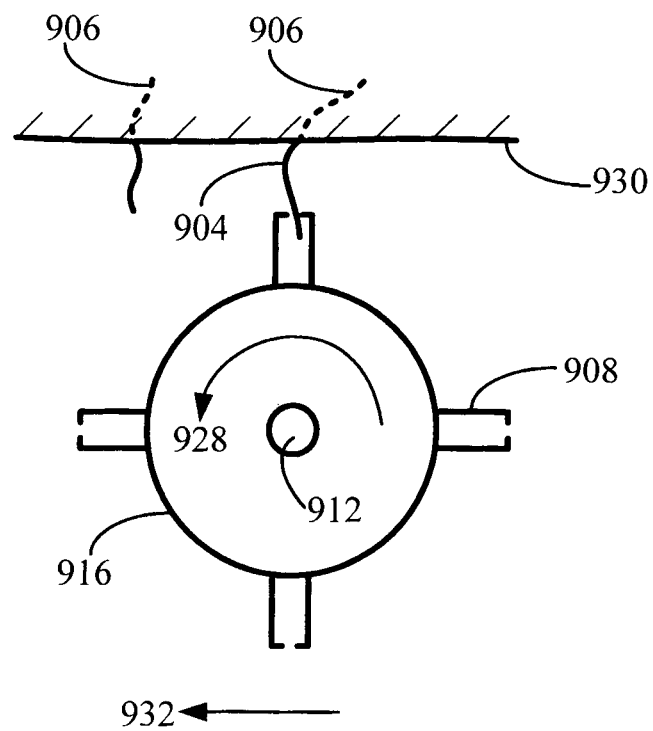
FIGS. 9 through 12 are schematic illustrations of the hair removal or shaving mechanism of the present apparatus for skin treatment and different states explaining the mechanism operation.
Figure 10:
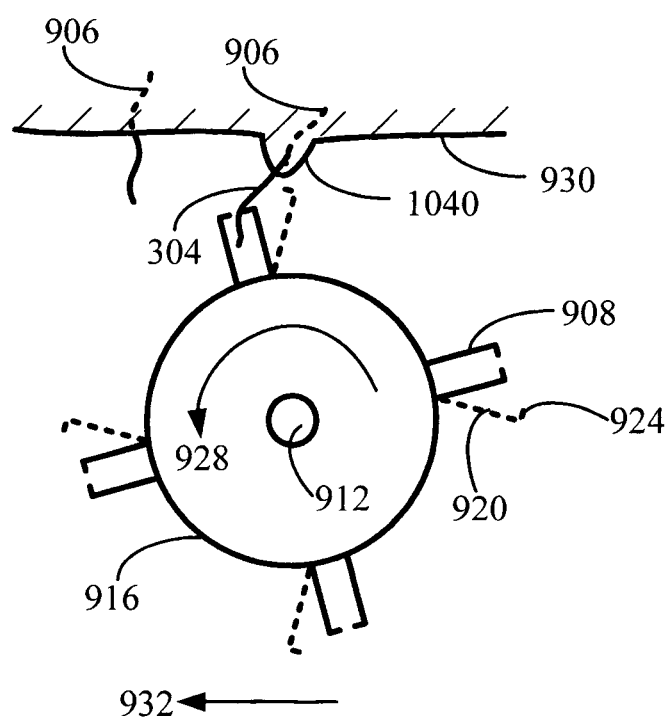

FIGS. 9 through 12 are schematic illustrations of the hair removal or shaving mechanism of the present apparatus for skin treatment and different states explaining the mechanism operation. FIG. 9 illustrates a first state of the operation of an exemplary hair removal mechanism in operation. FIG. 10 illustrates a second state of operation of the exemplary hair removal mechanism in operation. In the exemplary embodiment illustrated in FIG. 9, hair removal mechanism 900 may include at least one, and in some embodiments more than one, set of tweezers 908 attached to a holder 316 rotating around axis 912. Adjacent to tweezers 908 attached to the same axes is an optional lever 920 terminated by a blade 924. Alternatively, lever 920 may be rigidly coupled to tweezers 908 to ensure a constant follow-up after tweezers 908. There is a preset difference or offset between the location of tweezers 908 and the location of blades 924 of lever 920 with respect to skin 930. Typically, blade 924 would be located closer to skin 930 than tweezers 908. The difference in the location of blade 924 and tweezers 908 may be regulated according to the type of skin, hair, and particular treated segment of the subject casing.

For hair 904 removal, tweezers 908 are applied to skin 930. Holder 916 rotates in the direction indicated by arrow 928 and concurrently with rotation may move linearly on the surface of skin 930 in the direction indicated by arrow 932. As tweezers 908 continue to rotate to the second state, they pick-up at least one hair shaft or follicle 904 (FIG. 10) and begin pulling it out of skin 930. A pulling force generated by the rotation of tweezers 908 and assisted by linear movement of holder 916 applied to hair shaft 904 pulls together with hair shaft 904, skin 930 surrounding the hair shaft and follicle. This force deforms skin 930 and forms a type of goose bump or goose pimple 1040 protruding over the rest of the skin surface surrounding the follicle. Blade 924 cuts hair 904 (FIG. 11) substantially close to the peak of goose bump 1040. The pulling force is set to a particular tension with respect to the hair that is sufficient to tension the hair shaft but not to pull it out of the skin.

Figure 13:
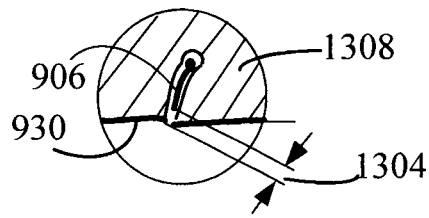
FIG. 13 is a magnified schematic illustration of a cut and retracted back hair follicle (shaft).

FIG. 13 is a magnified schematic illustration of a cut and retracted back hair shaft or follicle. Following the cut of hair shaft 904, skin 930 that formed goose bump 1040, retracts or returns to its normal at rest state. The residuals 906 of hair shaft 904 retract to the original position. The residual 906 of hair shaft 904 retracts deeper than skin surface or stratum corneum 930, such depth being indicated by numeral 1304, which marks the difference in the locations of the cut end of the residual 306 of the hair shaft 904 and skin surface 930. As can be seen in the figure, the end of the residual 906 resides substantially below skin surface 930. Numeral 1308 indicates the underlying tissue.

Figure 11:
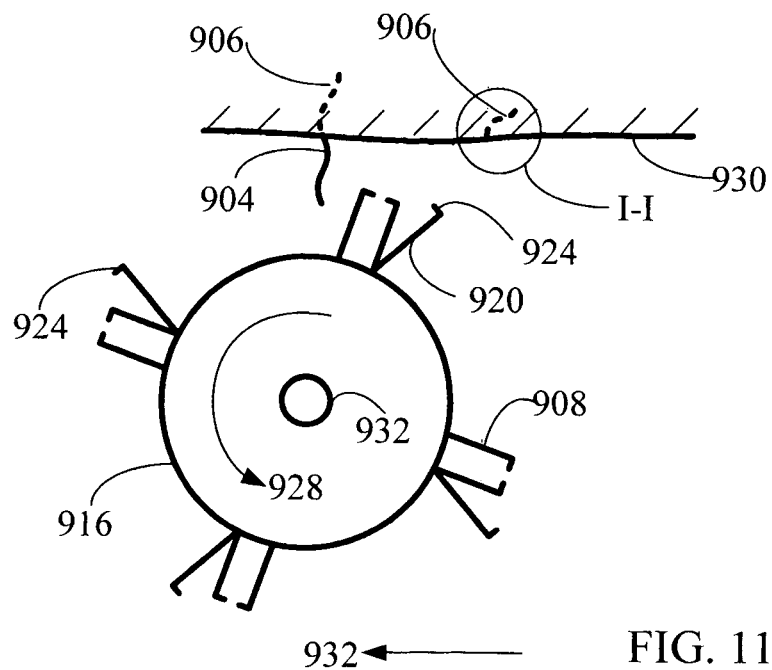
Figure 12:
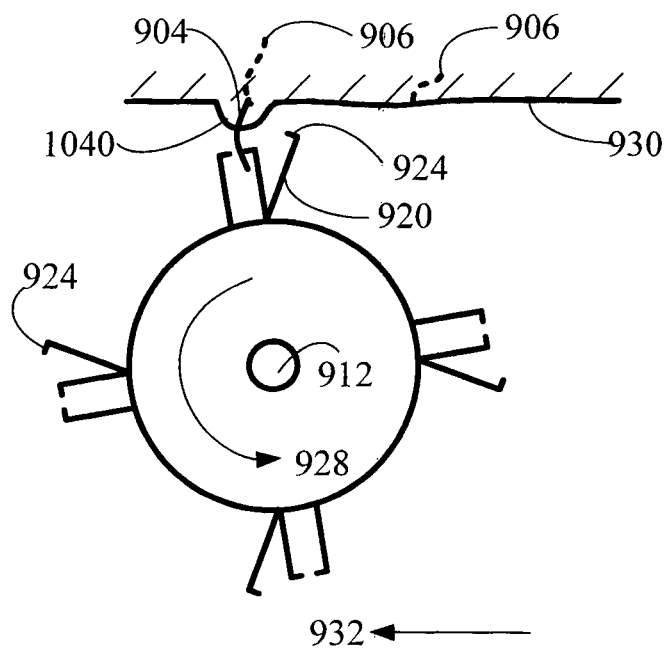

FIG. 11 illustrates a third state of the operation of the exemplary hair removal mechanism in operation. FIG. 12 illustrates a fourth state of operation of the exemplary hair removal mechanism. Holder 916 (FIGS. 11 and 12) continues to rotate in the direction indicated by arrow 928 and move linearly or in any other type of motion on the surface of skin 930 in the direction indicated by arrow 932. In the third state, tweezers 908 catch another hair shaft 904 and form bump 1040 in the fourth operational state in a way similar to the one explained above. Next, hair 904 is cut in a way similar to the way that the previous hair shaft was cut. The tweezers 908 and blades 924 may be orientated in the same direction or staggered and oriented in different directions. When some of the tweezers 908 and blades 924 are oriented in different directions, the user may move back along the earlier treated skin segment and still be efficacious. When tweezers 908 and blades 924 are orientated in the same direction the user at the end of treatment stroke may rotate applicator 104 (FIGS. 1 and 4) and move it in the opposite direction or simply reposition it to treat the next skin segment.

Alternatively, the hair removal mechanism 808 (FIG. 8) may be any one of the well-known mechanical hair removal mechanisms such as a razor, shaving, or an electric shaver such as for example, feminine electric shaver commercially available from Braun GmbH, Germany—model 3470 Softperfect. This model also includes other detachable heads of plucking and tweezing mechanisms. Similar or even the same mechanisms are also, of course, applicable to male hair removal/shavers. The illumination head/s may be attached and operate with a conventional shaver or epilator with only one head of either a shaver or epilator, or even a razor. The hair removal mechanism may be an interchangeable mechanism, where the mechanism most appropriate for the task is assembled on the applicator.

Figure 14:
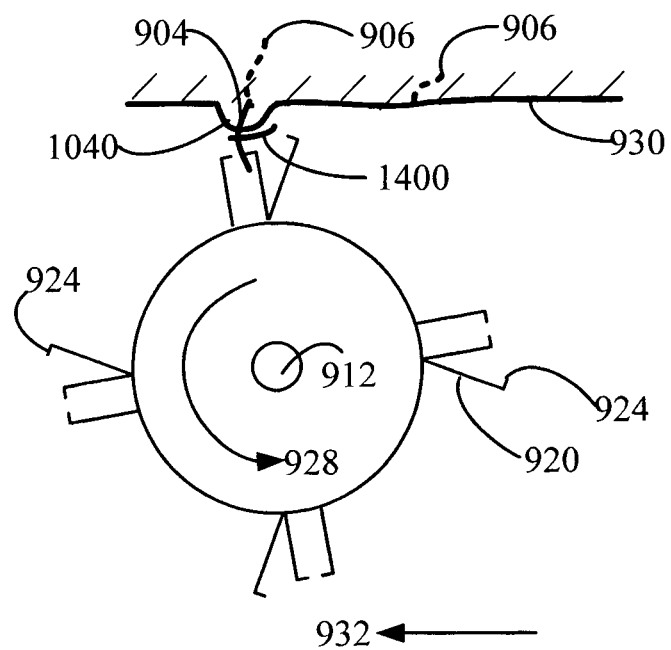
FIG. 14 is a schematic illustration of another exemplary embodiment of the hair removal mechanism of the applicator.

FIG. 14 is a schematic illustration of another exemplary embodiment of the hair removal mechanism. A comb type protective plate 1400 protects skin 930 and especially bumps 1040 from occasional damage by rotating blades 924 (FIG. 3). The comb type protecting plate 1400 may be attached to the applicator 104 or held independently by a user. Blades 924 may be replaced by a fixed blade, which would cut hair 904 pulled by tweezers 908. In such embodiments, holder 916 in addition to rotation may have a linear motion. Alternatively, two comb-like blades linearly sliding with respect to each other may be implemented to cut the hair.

Figure 15:
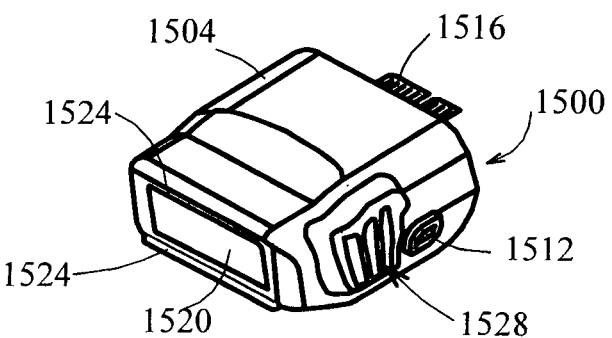
FIG. 15 is a schematic illustration of a three-dimensional view of an exemplary embodiment of a skin illumination module of the apparatus for personal skin treatment.

FIG. 15 is a schematic illustration of a three-dimensional view of an exemplary embodiment of a skin illumination module of the apparatus for personal skin treatment. Module 1500 includes a case 1504 incorporating one or more illumination sources, a pair of release buttons 1512 enabling easy illumination module release from the applicator, and a keyed connector 1516. A transparent protective window 1520 protects the illumination source. A pair of RF electrodes 1524 located along the protective window are operative to provide RF energy or radiation to the treated skin segment (not shown). In course of their operation the illumination sources emit large amount of heat. The heat as it will be explained in detail below is evacuated from the module by a cooling fluid flow or air generated by blower 712 (FIG. 7) through exhaust opening 1528. As explained above insertion of skin illumination or optical radiation providing module 1500 (FIG. 15), into its location in applicator 104 activates a module type detection mechanism. This prevents idle or erroneous operation of module 1500 and other skin treatment modules that the user may use. For example no high voltages will be present and "alive" in the RF electrodes 1524 of the module 1500 so that no one is subject to high voltage danger if the disposable cartridge is removed. As an additional safety measure, supply of RF energy to electrodes 1524 may be enabled only when both electrodes are applied to skin and the impedance between the electrodes is above certain threshold value. Module 1500 may be configured to operate as an illumination module only, as an RF energy applying module or both of them. In some embodiments a temperature sensor such as for example, a thermocouple may be mounted into one or both electrodes.

Figure 16:
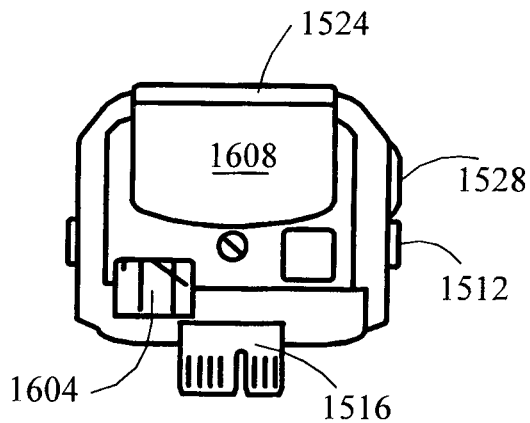
FIG. 16 is a schematic illustration of a rear view of the skin illumination module of FIG. 15.

FIG. 16 is a schematic illustration of a rear view of the skin illumination module of FIG. 15. In addition to the described earlier elements the FIG. shows cooling fluid intake opening 1604 through which the stream of cooling fluid, which may be air, enters module 1500 and is exhausted through exhaust opening 1528 (FIG. 15) and a rear side 1608 of a disposable cartridge containing one or more illumination or light sources.

Illumination module 1500 (FIG. 15) may include a variety of sources, a few non-limiting examples include an incandescent lamp, xenon lamp, laser diodes, LED, laser diodes or even a combination of two or more of these sources as well as other sources. The illumination sources may operate in a pulsed, continuous, graduated, modulated, oscillating or other operation mode as well as a combination of two or more of these modes. The power and operational times of the sources are selected to avoid potential damage to the treated segment of skin. In some embodiments each of the illumination sources may be packed in a cartridge-like packaging detachable from the illumination module 1500. The cartridge like packaging of the illumination source advantageously allows different illumination sources to be used with the same illumination module and applicator. The cartridge further includes a tag identifying the module and setting the module operational parameters. The tag may include a permanent data record which stores the type of the module, type of recommended treatment and recommended treatment parameters and a variable data record. The operational parameters may include optical and or RF power setting for fair or dark skin and for the various treatments which are each uniquely associated with the cartridge (e.g. cartridge type #1 for hair from fair skin removal, cartridge type #2 for hair from dark skin removal, cartridge type #3 for skin rejuvenation, cartridge type #4 for acne treatment, as well as other types of cartridges.) pulse duration and others. The variable data record enables recording the amount of events in course of which the module was operative. The data recorded into the tag enables upon the tag insertion into the applicator operation of the module. The tag may be an RFID, EEPROM, or a simple electronic circuit with unique characteristics such as resistance, capacitance, and others.

In some embodiments where it is desired or there exists a difference between the treatment parameters applicable to different skin types, the modules may be color coded facilitating easy distinction between them and avoiding erroneous use of the module.

Figure 18:
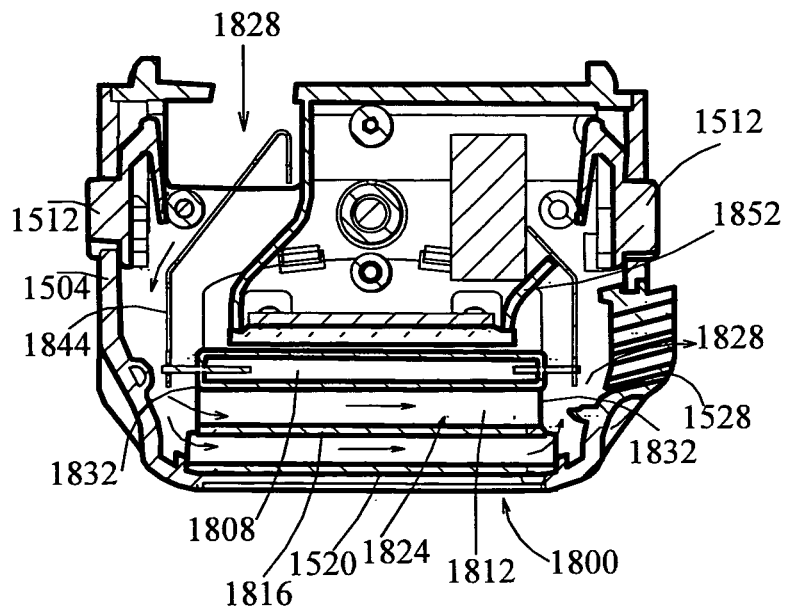
FIG. 18 is a schematic illustration of a cross section of the illumination module of FIG. 15 illustrating details of an exemplary embodiment of an illumination cartridge of the apparatus for personal skin treatment.
Figure 17:
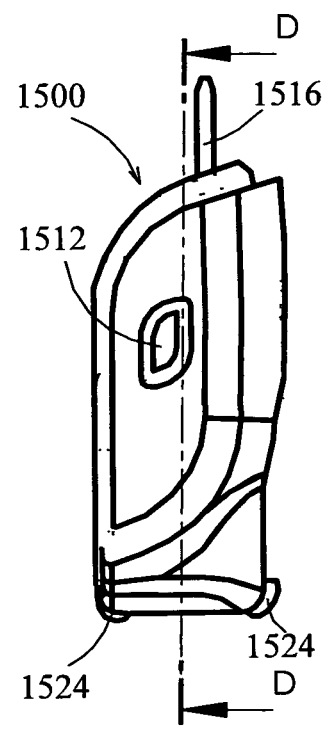
FIG. 17 is a schematic illustration of a side view of the illumination module of FIG. 15 of the apparatus for personal skin treatment.

FIG. 17 is a schematic illustration of a side planner view in the direction of arrow L of the illumination module of FIG. 15 and FIG. 18 is a cross section along plane D-D of the illumination module of FIG. 17 illustrating details of an exemplary embodiment of an illumination cartridge of the apparatus for personal skin treatment.

Disposable cartridge 1800 includes a source of optical radiation 1808, a reflector 1812 configured to reflect the emitted optical radiation to the segment of the skin (not shown) to be treated, and a dielectric coated protective window 1816. Window 1816 defines the aperture through which the optical radiation is emitted to the skin. The source of optical radiation 1812 may be an incandescent lamp such as AGAC 4627 high power density Xenon flash lamp commercially available from Perkin Elmer Optoelectronics Wenzel-Jaksch Str. 31 65199 Wiesbaden, Germany or any one of a group of LED, laser diode, solid state laser, a gas laser, or a Xenon IPL (Intense Pulsed Light) lamp.

Reflector 1812 is a prismatic case or a rectangular body with flat facets and polygonal cross section or a tubular cross section with an optional curvature of second or higher power. It may be a simple round cylinder cross section, a parabolic cross section or any other cross section allowing the optical radiation to be emitted across the aperture of window 1816 through which the optical radiation is emitted to the skin. The dielectric coating of window 1816 is selected such as to transmit the relevant sections of optical radiation spectrum to the treated segment of the skin and reflect the other. Reflector 1812 has butt end openings 1820 allowing air passage inside the reflector. The dielectric coated protective window 1816 located adjacent or attached to the open longitudinal section of reflector 1812 forms with the reflector 1812 an air-conducting channel 1824 bound on one side by reflector 1812 and on the other side by window 1816. A part of the stream of cooling air shown by arrow 1828 generated by a cooling fan 712 (FIG. 7) enters channel 1824 through butt end opening 1820 of reflector 1812. It is directed into the air-conducting channel 1824 along the source of optical radiation 1812 and cools it. Butt end openings 1820 of reflector 1812 terminate air-conducting channel on both of it ends and serve as cooling air exhaust openings. The area of reflector 1812 air exhaust openings 1528 is at least equal or larger to the area of openings 1820 allowing air passage into inner part of reflector 1812 and air conducting channel 1824. Optionally, a part of cooling air stream 1828 may be directed to flow around the external section of reflector 1812 and cools the outer section of reflector 1812.

According to some embodiments of the disclosure rotary blower 712 (FIG. 7) blows cooling air shown by arrows 1828 into one side of the disposable cartridge 1800 where the air flows in parallel (along) to the source of optical radiation 1808 and the reflector 1812 and emerges from the opposite side as shown by arrows 1828 of the optical radiation providing module 1800.

According to some embodiments of the disclosure, as also depicted schematically in FIG. 18, a second glass window 1520 is installed in parallel to window 1816 and part of the cooling air blown by the blower 712 and marked by arrow 1828 flows between the two windows 1520 and 1816. A slanted lamp electrode 1844, as shown in FIG. 18, may be installed on the air intake side of the optical radiation source 400, to enhance air flow in the direction of the windows. Arrows 1828 schematically illustrate the cooling air flow inside and outside reflector 1812 and between the windows 1520 and 1812. A bended support 1852 of reflector 1812 prevents return flow of hot air. Windows 1520 and 1838 may be made of Pyrex®, sapphire, quartz, or specially treated borosilicate glass. Window 1030 or both windows may be coated with a dielectric coating serving as a filter for reflecting back undesired wave lengths, such as UV and certain IR wavelengths, emitted from the optical radiation source 1808.

According to some embodiments of the disclosure, a thermal sensor, such as a thermistor or any other type of temperature measuring sensor may be installed on either inflow or the outflow end of the cooling air, as a safeguard against overheating in case of malfunction of the cooling means. Alternatively, temperature sensors may be installed in any other designated point in the cartridge and be operatively configured to sense the temperature in such designated point in the cartridge and communicate the temperature to the controller board 708 (FIG. 7). According to some embodiments of the disclosure, as also shown in FIG. 18, two reflectors may be mounted between the two windows (1520 and 1816), on both sides thereof, to prevent light scattering outside the treatment area. Alternatively, the disposable cartridge 1800 of applicator 104 may be made of a plastic material containing an amount of titanium dioxide ($TiO_2$) sufficient to disperse the reflected illumination.

The architecture of illumination or optical radiation providing module 1500 and method of cooling it allows a compact and effective optical radiation source to be produced and provide sufficient power for skin treatment. Module 1500 may operate in pulsed or continuous operation mode. It is known that low repetition rate optical radiation or light pulses are annoying the user who may be constantly visually tracking the applicator location. In order to ease the user's sensation, the optical radiation source may emit a number of low power light pulses interleaved between high power treatment pulses, increasing the repetition rate of the light pulses to a frequency of 16 Hz or more and alleviating the annoying and eye disturbing effects of low repetition rate light pulses.

According to some embodiments of the disclosure, an RFID device is connected to cartridge 1800 communicating with control circuit 708 (FIG. 7). The RFID device is preloaded with a maximal number of pulses to be emitted before the cartridge 1700 of illumination providing module 1500 has to be replaced and decreases the count with every emitted pulse. Alternatively, the RFID device is preloaded with a total energy that may be applied to the skin in a single treatment before the cartridge 1800 of the illumination providing module 1500 (FIG. 15) has to be replaced. The RFID device may also serve as an additional safety measure, where the control circuit 708 prevents the radiation providing module 1500 from emitting pulses if the RFID is not identified, namely the optical radiation or illumination providing module 1500 has not been installed correctly.

In an additional embodiment, a 1024 Bit 1-Wire EEPROM such as DS2431 commercially available from Maxim/Dallas Semiconductors, Inc., Sunnyvale, Calif. 94086 U.S.A. 1-Wire EEPROM operating as a counter can be assembled on the control printed circuit 708 that among others controls the radiation providing module 1500. Similar to the RFID the counter may be pre-loaded with the desired information. The same 1-Wire EEPROM may function for radiation providing module 1500 authenticity identification.

Figure 19:
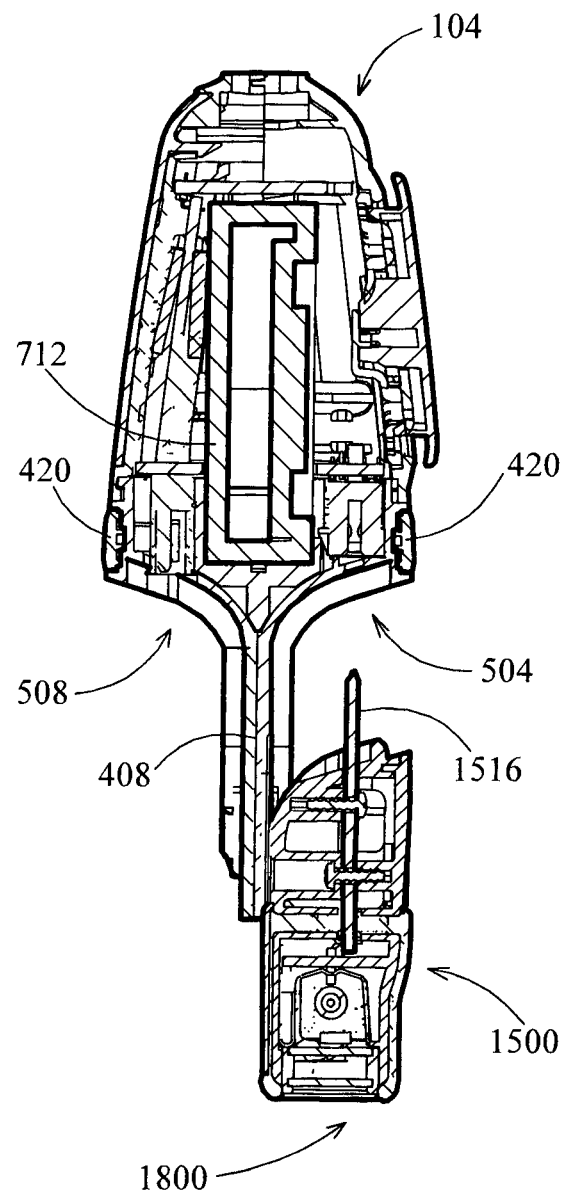
FIG. 19 is a schematic illustration of a cross section of an exemplary embodiment of the applicator with illumination module of the apparatus for personal skin treatment.

FIG. 19 is a schematic illustration of a cross section of an exemplary embodiment of the applicator with illumination module of the apparatus for personal skin treatment. In use illumination module 1500 containing one or more illumination sources is inserted into a receiving bay 504 of the applicator 104. Keyed connector 1516 ensures that only compatible modules could be inserted into receiving bay 504 of applicator 104.

Figure 20:
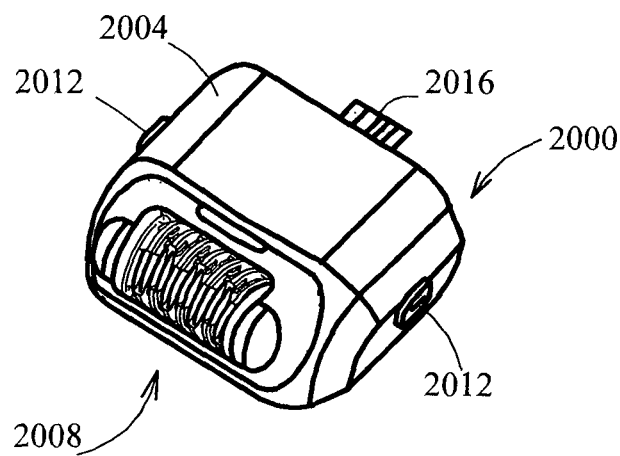
FIG. 20 is a schematic perspective illustration of an exemplary embodiment of the epilator module of the apparatus for personal skin treatment.

FIG. 20 is a schematic perspective illustration of an exemplary embodiment of the epilator module of the apparatus for personal skin treatment. Epilator module 2000 includes a case 2004 incorporating a hair epilating or hair removal mechanism 2008 to be disclosed in detail below, a pair of release buttons 2012 enabling easy epilator module release from the applicator, a keyed connector 2016, and a tag identifying the module and setting the module operational parameters. The tag may be an RFID, EEPROM, or a simple electronic circuit with unique characteristics such as resistance, capacitance, and others. The epilator mechanism may be such as Silk-epil, commercially available from Braun GmbH, Germany.

Figure 21:
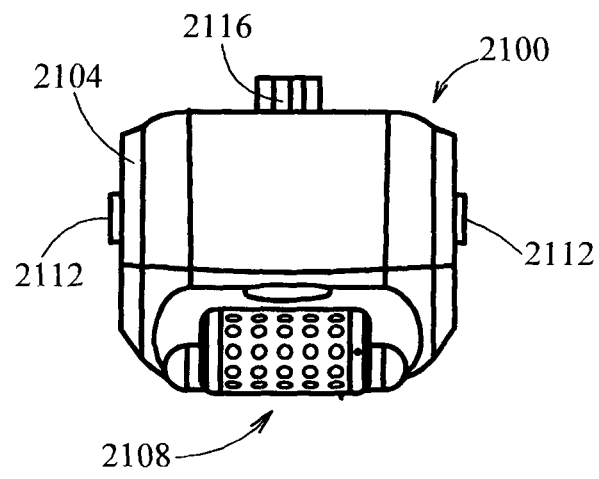
FIG. 21 is a schematic illustration of a frontal view of an exemplary embodiment of a skin rejuvenation module of the apparatus for personal skin treatment.

FIG. 21 is a schematic illustration of a frontal view of an exemplary embodiment of a skin rejuvenation module of the apparatus for personal skin treatment. Skin rejuvenation module 2100 includes a case 2104 incorporating a matrix of skin rejuvenating electrodes 2108, a pair of release buttons 2112 enabling easy epilator module release from the applicator, a keyed connector 2116, and a tag identifying the module and setting the module operational parameters. The tag may be an RFID, EEPROM, or a simple electronic circuit with unique characteristics such as resistance, capacitance, and others. As it will be explained below skin abrasion module 2300 (FIG. 23) may also be used for skin rejuvenation.

Figure 22:
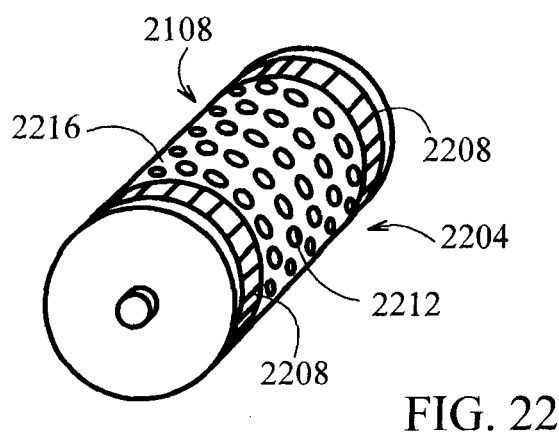
FIG. 22 is a schematic illustration of an exemplary embodiment of the skin rejuvenation electrodes of the skin rejuvenation module of the apparatus for personal skin treatment.

FIG. 22 is a schematic illustration of an exemplary embodiment of the skin rejuvenation electrodes of the skin rejuvenation module of the apparatus for personal skin treatment.

The skin rejuvenation electrode 2108 disclosed in detail in U.S. patent application Ser. No. 12/505,576 to the same assignee filed on Jul. 20, 2009, is a segmented electrode and it includes a central segment 2204 being in size of about 15 to 20 mm wide and two peripheral segments 2208 arranged along the circumference/perimeter of segment 2204. Central segment 2204 is populated by a plurality of small terminated by a spherical shape or flat RF providing electrodes 2212. Thermal and electrical insulation 2216 between central segment 2204 and peripheral segments 2208 is also illustrated. Typically, the thermal and electrical insulation is about 0.5-1.0 mm wide. In the current embodiment of the segmented RF electrode, the peripheral segments 2208 about 2 to 4 mm wide and are made of a thermally conductive material. Electrodes 2212 are made of electrically conductive material and electrodes 2208 are made of electrically conducting or ceramic material. In particular, the tested segments 2208 of the electrodes were made of materials selected from a group consisting of metal oxides or Ceramics. Aluminum nitride, Boron nitride, and similar are examples of such materials. Electrode 2108 may be of rectangular, elliptical or other suitable shape or even a flat surface. Electrodes 2208 may have uniform width or sections of different width. In some embodiments the electrodes may be coated by a dielectric coating. RF source may provide RF energy to the electrodes and a thermal sensor may be incorporated in each of the electrodes.

Figure 23:
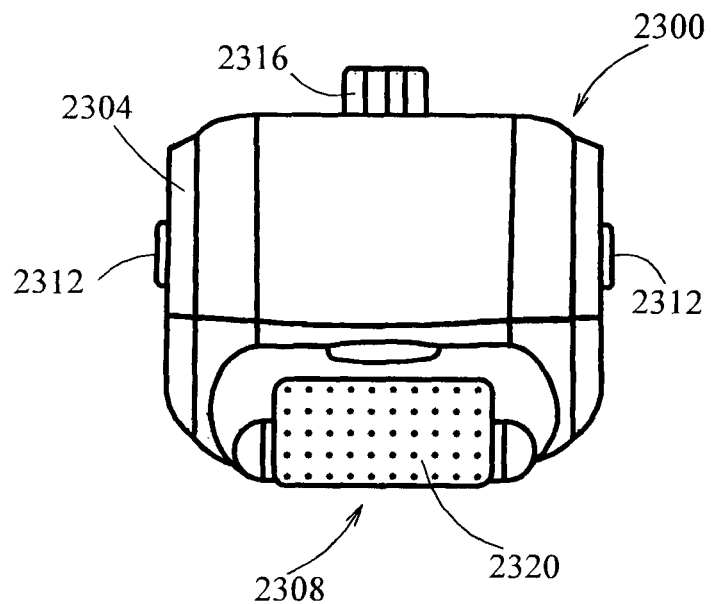
FIG. 23 is a schematic illustration of a frontal view of an exemplary embodiment of a skin abrading module of the apparatus for personal skin treatment.

FIG. 23 is a schematic illustration of a frontal view of an exemplary embodiment of a skin abrading module of the apparatus for personal skin treatment. Skin abrading module 2300 includes a case 2304 incorporating a skin abrading roll 2308, a pair of release buttons 2312 enabling easy abrading module release from the applicator, a keyed connector 2316, and a tag identifying the module and setting the module operational parameters. Skin abrading roll 2308 may be a metal or plastic roll coated with fine diamond powder or by fine ScotchBright™ type material. Alternatively, abrading roll 2308 may be a soft material roll coated by fine Scotch-Bright™ type material or completely made of a Scotch-Bright™ type material.

A DC motor and a gear mounted in the inner compartment of case 2304 provide rotation to skin abrading roll 2308. As the user moves the skin abrading module 2300 along the treated skin segment, skin abrading roll 2308 may rotate such that linear speed of surface 2320 of skin abrading roll 2308 would be greater or smaller than the speed with which user displaces the skin abrading module 2300. In one embodiment, skin abrading roll 2308 may rotate in a direction where the linear speed of surface 2320 matches the skin abrading module 2300 displacement direction. In another embodiment, skin abrading roll 2308 may rotate in a direction where the linear speed of surface 2320 is oriented in a direction opposite to the skin abrading module 2300 displacement direction.

In an additional embodiment, skin abrading roll 2308 may be replaced by two or more diamond coated or Scotch-Bright™ coated rolls rotating with different speed and pulling in between then different segments of treated skin. Abraded, dead, or flat stratum corneum skin cells may be removed later by a soft pad and a skin cooling lotion or cream. Alternatively, skin abrading module 2300 may have a vacuum slit or vacuum openings implemented in the skin abrading roll that would remove by suction abraded stratum corneum particles.

The friction between the skin abrading roll 2308 and the skin is high and it develops forces that in addition to removal of the stratum corneum may cause displacement of the abrading module over the treated skin segment. Displacement speed monitoring arrangement mounted on controller board 708 (FIG. 7) could be in communication with the controller controlling module 2300 movement and set a proper displacement speed, leaving to the user discretion application of proper for particular treatment pressure.

Figure 24:
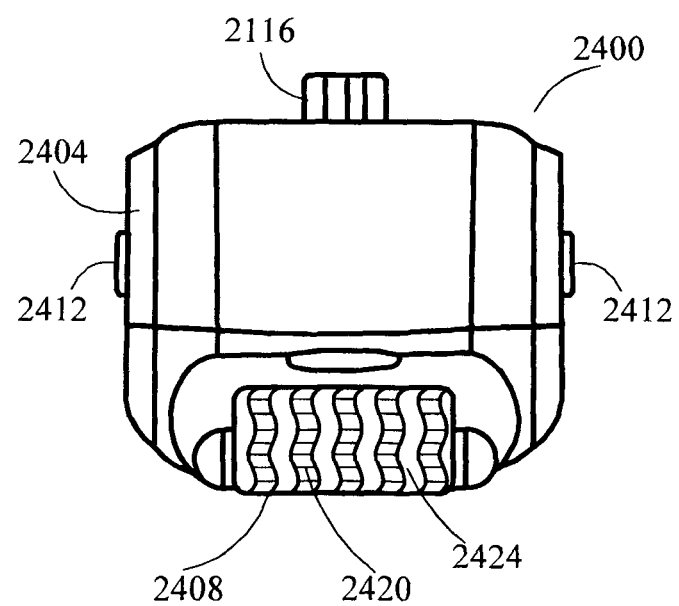
FIG. 24 is a schematic illustration of a frontal view of an exemplary embodiment of a skin massaging module of the apparatus for personal skin treatment.

FIG. 24 is a schematic illustration of a frontal view of an exemplary embodiment of a skin massaging module of the apparatus for personal skin treatment. Skin massaging module 2400 includes a case 2404 incorporating a skin massaging roll 2408, a pair of release buttons 2412 enabling easy massaging module release from the applicator, a keyed connector 2416, and a tag identifying the module and setting the module operational parameters. Skin massaging roll 2408 may be a metal or plastic roll in which a series of grooves 2420 and protrusions or ribs 2424 is made. In one embodiment, roll 2408 may have a type of braking mechanism resisting displacement of skin massaging module 2400 across the treated skin segment. In course of module 2400 displacement, skin enters grooves 2420 and is massaged by protrusions 2424.

Alternatively, a DC motor and a gear mounted in the inner compartment of case 2404 may provide rotation to skin massaging roll 2408. The rotation speed of roll 2408 may be selected such as to enable pull of the skin into grooves 2420.

Figure 25A:
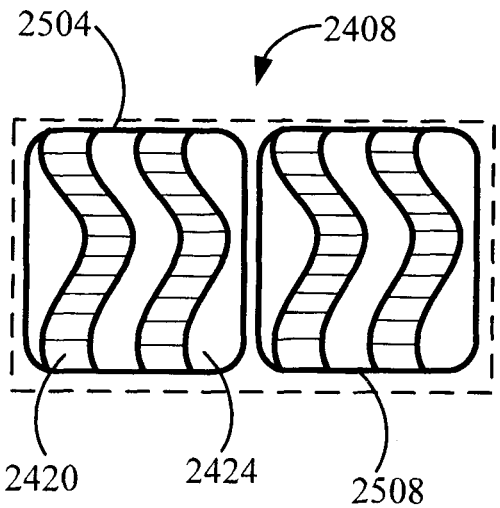
FIG. 25 is a schematic illustration of another exemplary embodiment of the skin massaging roll of the skin massaging module of the apparatus for personal skin treatment.
Figure 25B:
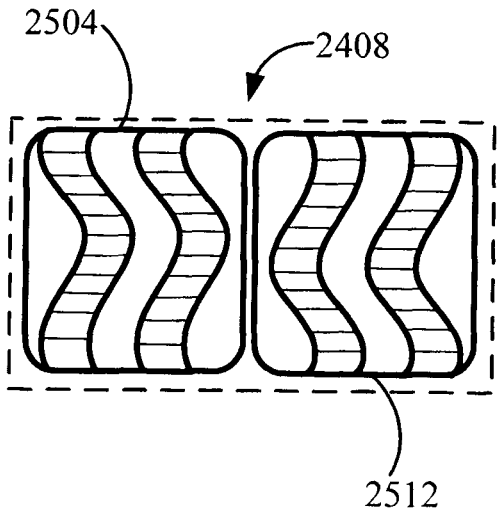

FIG. 25 is a schematic illustration of another exemplary embodiment of the skin massaging roll of the skin massaging module of the apparatus for personal skin treatment. Skin massaging roll 2408 may be a single roll or an assembly of two or more rolls 2504 and 2408. Rolls 2504 and 2508 may have identical protrusions 2420 and grooves 2424. Alternatively, as shown in FIG. 25b) rolls 2504 and 2512 may have protrusions directed in opposite direction. Each of the rolls may rotate at a different speed enhancing the skin massaging action.

Figure 26A:
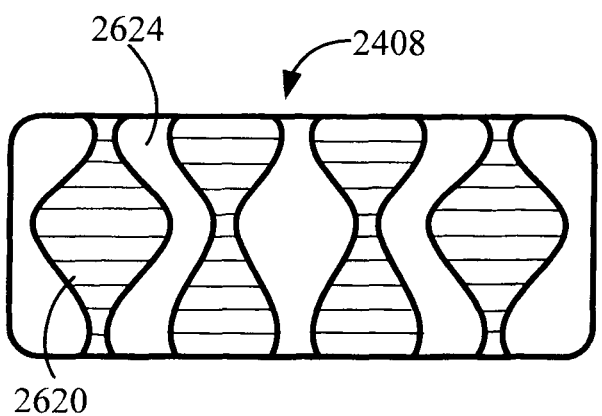
FIG. 26 is a schematic illustration of an additional exemplary embodiment of the skin massaging roll of the skin massaging module of the apparatus for personal skin treatment.
Figure 26B:
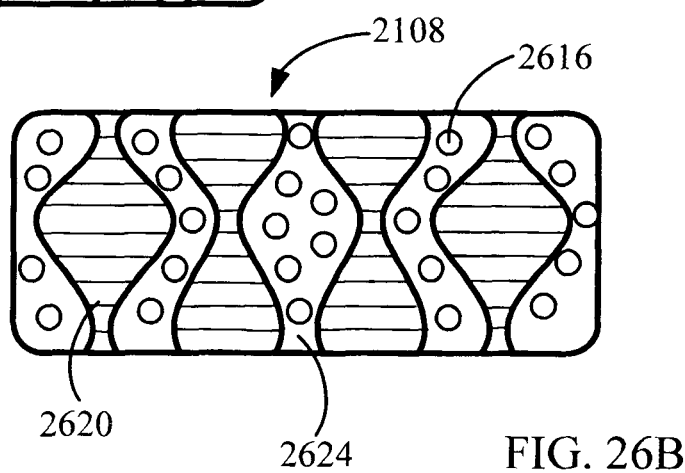

FIG. 26 is a schematic illustration of an additional exemplary embodiment of the skin massaging roll of the skin massaging module of the apparatus for personal skin treatment. Roll 2108 includes a plurality of vacuum openings 2616 operative to suck the skin into grooves 2624 between protrusions 2420 further enhancing the massaging action of the skin massaging module 2400. As explained above the massaging module may be implemented to support a difference in the linear speed of the massaging roll 2408 and the speed applicator 104 displacement over the skin. This may further enhance the massaging action.

One of the interchangeable modules may be an ultrasound providing module. Provisional Patent application Ser. No. 61/248,997 filed on Oct. 6, 2009 to the same assignee discloses such a module and a method of ultrasound to skin application, where the transducers are positioned at a predetermined distance from each other on opposing borders of an area of skin being treated and at a predetermined angle relative to the surface of the skin. The angle between the transducers is maintained by a wedge made of a sound index-matching material as known in the art. The distance between the transmitter and receiver is dependent on the thickness of the tissue at the area to be treated. The transducers are operative to emit ultrasound beams, commonly in pulse form, at an angle relative to the surface of skin to be treated so that a portion of the emitted beams impinge upon skin tissue at a Brewster's angle of incidence, and follow propagation path, which is generally parallel to the surface of the skin through treated area producing a desired skin treatment effect.

Figure 27:
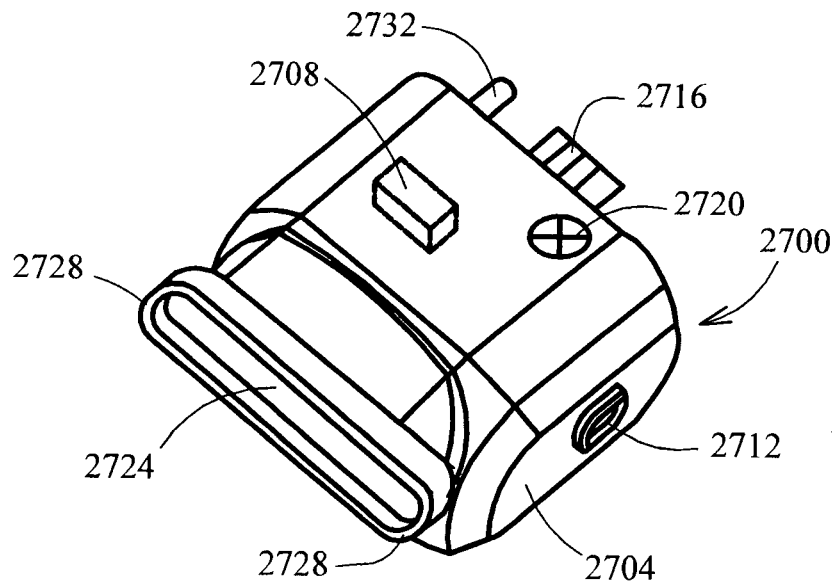
FIG. 27 is a schematic perspective illustration (of a frontal view) of an exemplary embodiment of a vacuum module of the apparatus for personal skin treatment.
Figure 28:
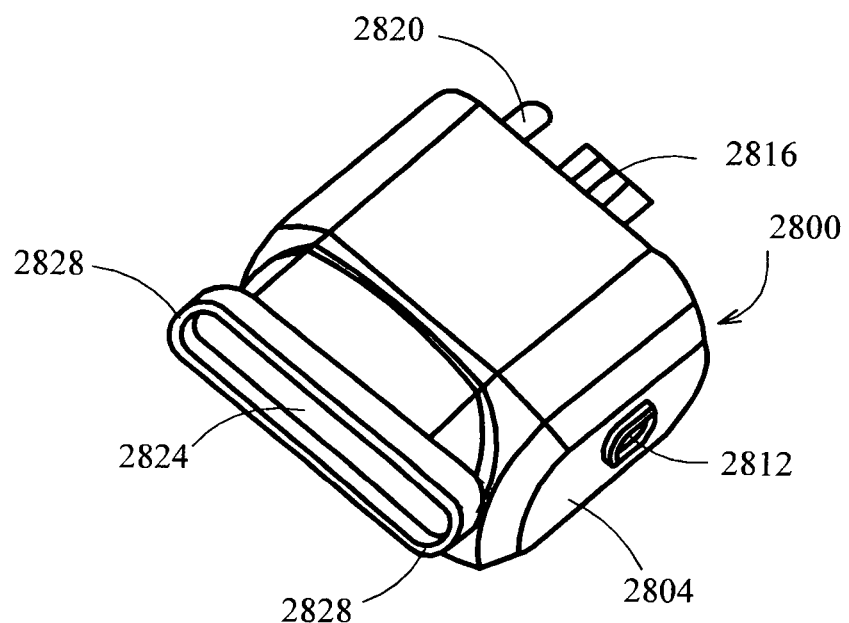
FIG. 28 is a schematic perspective illustration of another exemplary embodiment of a vacuum module of the apparatus for personal skin treatment.

FIG. 27 is a schematic perspective illustration (of a frontal view) of an exemplary embodiment of a vacuum module of the apparatus for personal skin treatment. Module 2700 includes a case 2704 incorporating a miniature vacuum pump 2708, a pair of release buttons 2712 enabling easy vacuum module release from the applicator, a keyed connector 2716 through which power is supplied to the miniature vacuum pump and identifying and proper locating the module, and a tag 2720 identifying the module and setting the module operational parameters. The tag may be an RFID, EEPROM, or a simple electronic circuit with unique characteristics such as resistance, capacitance, and others. Suction opening 2724 is surrounded by a suction cup 2728 attaching the module to the skin surface. Cup 2724 may be made of a soft antiallergenic material such as polyurethane, silicone, or similar. Vacuum suction removes from the skin for example, abraded epidermis particles, acne, black and white heads, and other debris. The exhausted air is evacuated from the module through an exhaust tube 2732 communicating with vacuum pump 312 (FIG. 30) through opening 606 (FIG. 6). The sucked in debris is retained inside module 2700 and disposed upon completion of the treatment. In an additional embodiment, the debris may be collected in the docking unit 108 (FIGS. 1 and 3) and disposed periodically. In an additional embodiment the debris may be evacuated through exhaust tube 2732 with the rest of the air, in the simplest form. The level of vacuum is selected to cause the desired effect and still enable continuous displacement of the applicator over the skin surface. Module 2700 across the skin displacement allows gentle massaging of the treated skin area and thus loosens/softens the acne blackheads or the whiteheads from the root The module 2700 can be a disposable module FIG. 28 is a schematic perspective illustration of another exemplary embodiment of a vacuum module of the apparatus for personal skin treatment. Module 2800 includes a case 2804, a pair of release buttons 2812 enabling easy module release from the applicator, and a keyed connector 2816. In some embodiments connector 2816 is a dummy connector. It does not convey electric signals and serves mainly as means to stabilize the module in place. In another embodiment where a tag identifying the module and setting the module operational parameters is included in the module, connector 2816 may carry electrical signals from the tag. A connecting tube 2820 enables vacuum module 2800 through opening 606 (FIG. 6) connection to vacuum pump 312 (FIG. 3). Suction opening 2824 is surrounded by a suction cup 2828 attaching the module to the skin surface. Cup 2824 may be made of a soft antiallergenic material such as polyurethane, silicone, or similar. Vacuum suction removes from the skin for example, abraded epidermis particles, acne, black pimples and others. Collected debris may be retained inside module 2800 and the sucked-in air may be evacuated from the module through a regular exhaust opening in docking station 108 (FIGS. 1 and 3). Alternatively, the debris may also be evacuated through a regular exhaust opening in the docking station. Module 2800 may be implemented as a disposable module.

Figure 29:
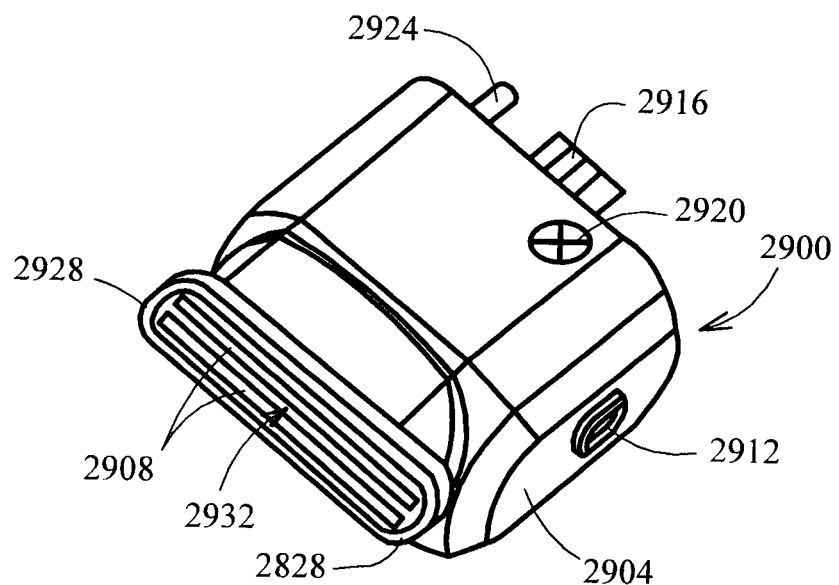
FIG. 29 is a schematic perspective illustration of an exemplary embodiment of a combined RF and vacuum module of the apparatus for personal skin treatment.

FIG. 29 is a schematic perspective illustration of an exemplary embodiment of a combined RF and vacuum module of the apparatus for personal skin treatment. Module 2900 includes a case 2904 incorporating a pair of RF electrodes 2908 operative to couple RF energy to the treated segment of skin, a pair of release buttons 2912 enabling easy module 2900 release from the applicator, a keyed connector 2916, and a tag 2920 identifying the module and setting the module operational parameters. The tag may be an RFID, EEPROM, or a simple electronic circuit with unique characteristics such as resistance, capacitance, and others. Suction opening 2932 is surrounded by a suction cup 2928 attaching the module to the skin surface. Cup 2928 may be made of a soft antiallergenic material such as polyurethane, silicone, or similar. A connecting pipe or tube 2924 enables vacuum module through opening 606 (FIG. 6) to vacuum pump 312 (FIG. 3) connection. Vacuum suction may remove from the skin abraded epidermis particles, acne, black and white heads, and others. The level of vacuum is selected to cause the desired effect and still enable continuous displacement of the applicator over the skin surface. This module displacement allows gentle massaging of the treated skin area assisting in acne removal and other procedures.

Figure 30:
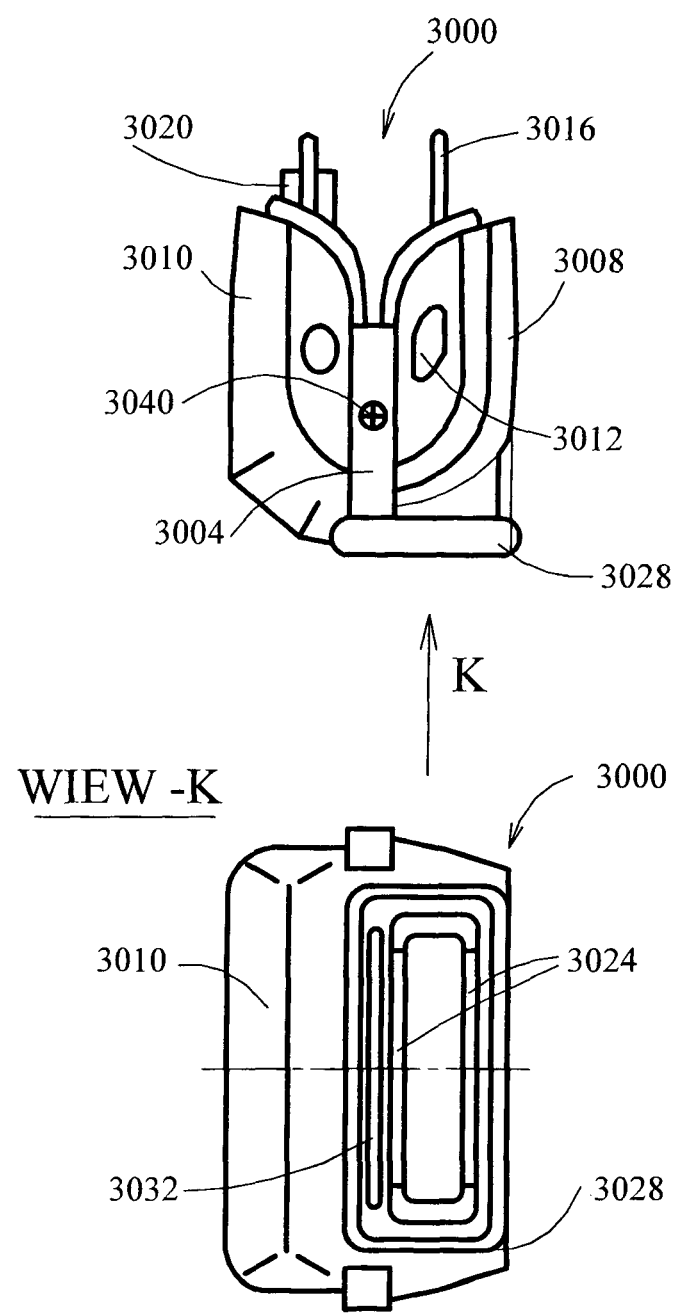
FIG. 30 is a schematic illustration of an exemplary embodiment of a combined illumination, RF, and vacuum module of the apparatus for personal skin treatment.

FIG. 30 is a schematic illustration of an exemplary embodiment of a combined illumination, RF, and vacuum providing module of the apparatus for personal skin treatment. Module 3000 may be implemented as a combination of the illumination cartridge 1500 and vacuum module 2700 or 2800. Module 3000 includes a case 3004 incorporating an illumination module 3008 with the illumination cartridge operative to couple illumination to the treated segment of the skin and vacuum module 3010. Cartridge 3008 is generally similar to cartridge 1500, although the dimensions and configuration may be different. Cartridge 3008 includes a pair of RF electrodes 3024 similar to electrodes 1524 (FIG. 15) of cartridge 1500 operative to couple RF energy to the treated skin segment, a pair of release buttons 3012 enabling easy module 3000 release from the applicator, and a keyed connector 3016. Cartridge 3008 may be surrounded by a suction cup 3028 with vacuum openings 3032 communicating through module 3010 and vacuum connecting tube or pipe 3020 through opening 606 (FIG. 6) to vacuum pump 312 (FIG. 3). When vacuum is supplied to suction cup 3028 it operates to attach module 3000, or more specifically, attach module 3008 to the skin surface. Cup 3028 may be made of a soft antiallergenic material such as polyurethane, silicone, or similar. Vacuum suction removes for example, abraded epidermis particles, acne, black and white heads, and others. The vacuum is beneficial not only in removing the debris. It's also beneficial in the coupling of optical and RF energy to the tissue. The level of vacuum is selected to cause the desired effect and still enable continuous or step like displacement of the applicator over the skin surface. Module 3000 displacement allows gentle massaging of the treated skin area assisting in acne removal. Vacuum also stretches the skin being in contact with the protective glass of illumination module 3008. This increases the efficiency of the illumination by reducing illumination scattering present when a gap between the protective glass and the skin exists as well as scattering by the dermal structure of the skin. Module 3000 is a combination of a disposable illumination cartridge and a disposable vacuum cartridge and as such may be implemented as a disposable module. Additionally, cup 3028 may be implemented as a disposable cup. Module 3000 may include a tag 3040 identifying the module and setting the module operational parameters. The tag may be an RFID, EEPROM, or a simple electronic circuit with unique characteristics such as resistance, capacitance, and others.

Figure 31:
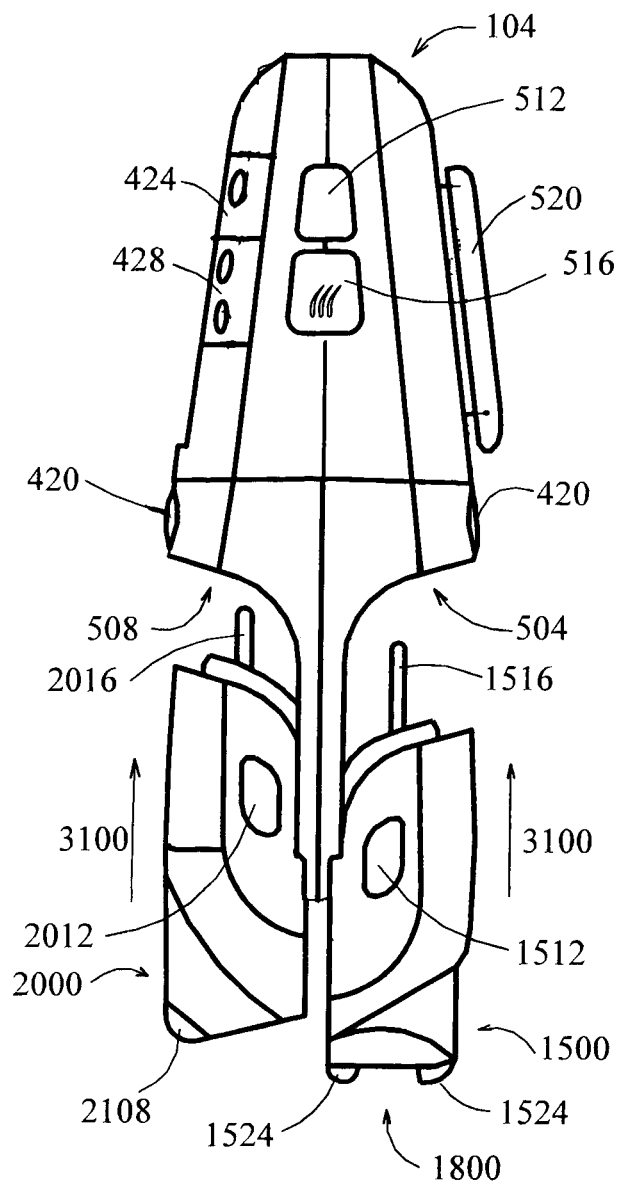
FIG. 31 is a schematic illustration of an exemplary embodiment of the applicator with an illumination module and an epilator module of the apparatus for personal skin treatment.

FIG. 31 is a schematic illustration of an exemplary configuration of the applicator with an illumination module and an epilator module of the apparatus 100 (FIG. 1) for personal cosmetic skin treatment. For coupling to the applicator 104 modules 1500 and 2000 are slid as shown by arrow 3100 into their respective receiving bays 504 and 508 and positively fixed in their locations. Electronics located on printed circuit board 708 (FIG. 7) recognizes the identification tag of the module and sets its operating parameters. Applicator 104 is now ready for use and set to perform at least two procedures, as will be explained below, enabled by the inserted modules. In order to exchange a module the user presses release buttons 1512 or 2012 extracts the earlier inserted module and inserts a different desired module.

In a similar way the user may assemble any other combination of different modules and perform different cosmetic skin treatment.

Figure 32:
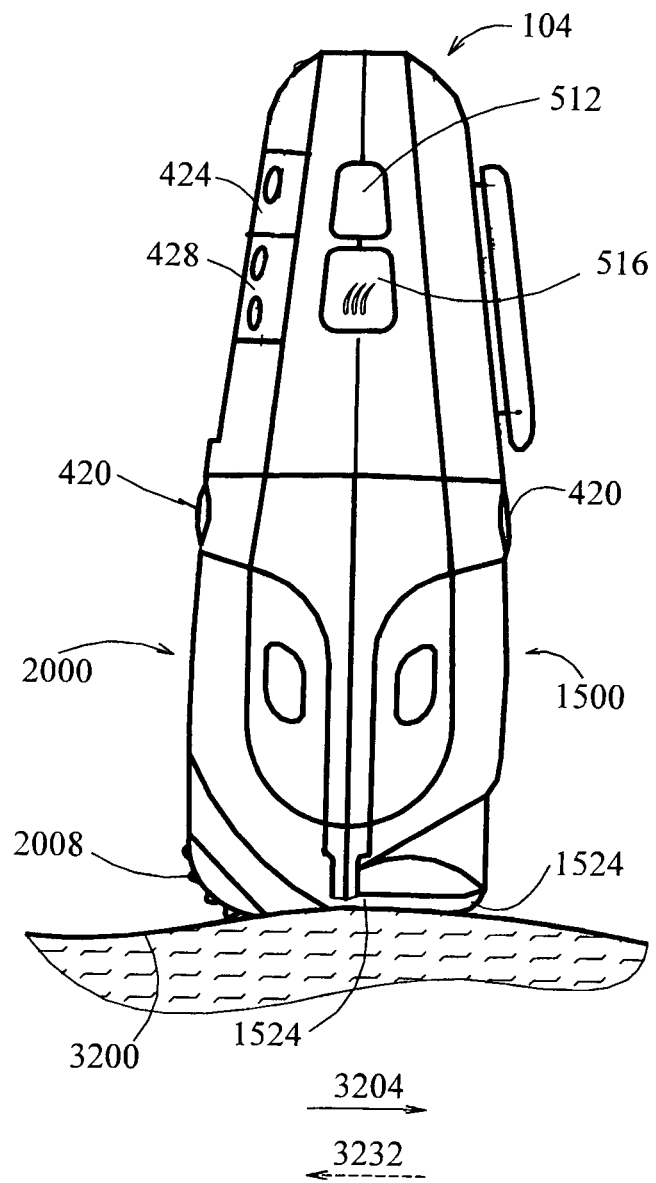
FIG. 32 is a schematic illustration of an exemplary method of skin treatment using the present applicator/device and apparatus.

FIG. 32 is a schematic illustration of an exemplary method of cosmetic skin treatment using the present applicator/device and apparatus. For skin treatment, applicator 104 is applied to a segment of skin 3200 to be treated, enabling firm or at least mostly firm contact between the RF electrodes 1524 (FIG. 15) and the skin. Optical radiation providing module 1500 is activated and it illuminates the skin section to be treated and the RF energy supplied to the electrodes 1524 weakens hair roots and hair follicle or even destroys them. The user or a built-in mechanism for continuously displacing the device across the skin displaces device 104 in a desired direction indicated by arrow 2404, for example, along the segment of the skin to be treated. In one embodiment, optical radiation is directed through aperture of illumination cartridge 1500 to irradiate a segment of skin 3200 to be treated by a constant optical radiation power and RF energy, both set by the appropriate module identification tag and supplied in continuous or pulsed mode, and the applicator 104 is displaced along the skin segment to be treated in the direction of arrow 3204.

Displacement speed monitoring arrangement mounted on controller board 708 (FIG. 7) may set a proper displacement speed. The displacement speed-optical radiation power or RF energy dependence may be prepared and loaded as a look-up-table (LUT) into control circuit 708 or 300. As the treatment progresses and device 104 advances across the skin, it reaches the border of the skin segment to be treated. As device 104 reaches the end of the treated or shaved skin segment, the user manually repositions device 104 on the next segment of skin to be treated or on another non-treated segment of the skin and sets it for displacement into the same or opposite direction. The danger of causing skin burns by treating the same segment of skin twice is reduced, since there is some time for the skin to cool down between successive skin treatments by device 104. Optical radiation coupled with the RF energy retards future hair growth on the treated segment of the skin by heating hair follicle. RF energy applied to the same skin segment also heats deeper skin layers where hair bulbs and follicles are located, enhancing the hair removal process performed by the optical radiation. Weakened hair may be easier removed by an epilator module 2000 that follows the illumination module.

Some skin pretreatment operations such as skin cleaning performed by water and soap or other cleaning means, may be introduced. The frequency of the RF energy applied for the skin treatment is typically in the range of 6.0 MHz to 7.0 MHz and generally does not require application of gel improving electric contact between electrodes 1524 and skin 3200.

In an additional exemplary method of skin treatment using the present device and apparatus, the user applies the applicator or skin treatment device 104 to a skin segment from which hair has to be removed. The epilator is moved in the direction indicated by arrow 3232 and the hair is removed from the skin segment by mechanical means, for example by epilator module 2100. Following mechanical hair removal, optical radiation of proper power and wavelength is applied to the same segment of skin that was treated. Optionally, RF energy may be applied to the same segment of skin. Application of optical radiation and RF energy retards further hair growth. Similar to the earlier disclosed method the user displaces the applicator 104 or the applicator displacement mechanism displaces itself automatically from a treated skin segment to another untreated skin segment.

Figure 33:
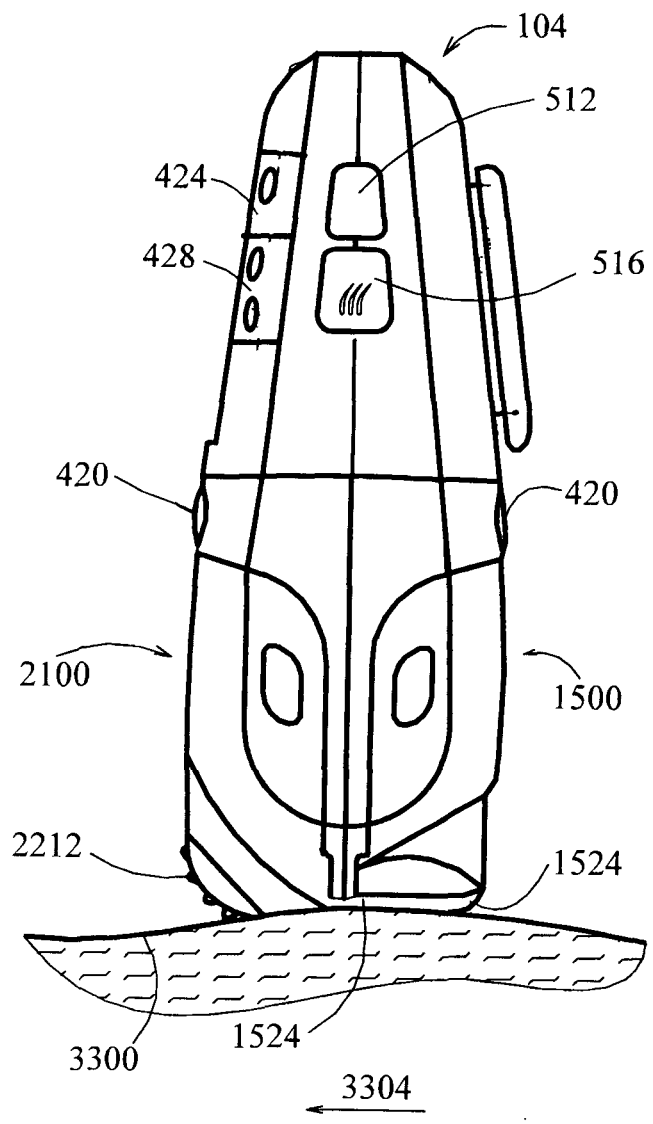
FIG. 33 is a schematic illustration of another exemplary method of skin treatment using the present applicator/device and apparatus.

FIG. 33 is a schematic illustration of another exemplary method of skin treatment using the present applicator and apparatus. For skin rejuvenation treatment, applicator or device 104 is applied to a segment of skin 3300 to be treated, enabling firm or at least mostly firm contact between the RF electrodes 1524 and the skin 3300. The user, or a built-in mechanism for continuously displacing the device across the skin, displaces device 104 in a desired direction indicated by arrow 3304, for example, along the segment of the skin to be treated. RF energy is applied to electrodes 2208 and 2212 (FIG. 22) of the skin rejuvenation module 2100. It is well known that stratum corneum, the upper skin layer, is a dielectric and until certain voltage stressing it beyond its dielectric strength is applied to it, the stratum corneum resists electrical breakdown. As the RF voltage supplied by source of RF voltage exceeds the electrical breakdown threshold, an electrical discharge takes place. The absence of a conductive fluid between the skin 2504 and the electrodes 2208 and 2212 of the applicator 104 allows the device to achieve a higher skin break-down potential and prevents the occurrence of a short circuit between the individual voltage supplying elements 2212.

The absence of a conductive fluid also facilitates limiting fractal skin damage caused by the RF voltage or energy radiating from the dome type contacts 2212 to the skin contact points only. The discharge ablates the stratum corneum and since the coupling between voltage supplying elements terminated by domes 2212 and the skin 2500 is a conductive coupling, it enables electric current flow from the apex of dome 2212 to highly conductive epidermis and dermis and deeper located skin layers. Enabled by skin breakdown, electric current heats and coagulates some of the target section of skin 2800 volume initially in contact with the domes 2212 and in immediate vicinity of domes 2212 generating an array or matrix of microscopic skin wounds. The dome shaped form of the voltage applying elements 2212 facilitates electric discharge that takes place between the apex of the dome shaped elements 2212 and contact spot on the skin 3200. The domes 120 however, do not penetrate the skin. Healing of these wounds rejuvenates (tightens) the damaged skin segment and reduces or removes wrinkles existing at this skin segment. The illumination module 1500 may be equipped by a source of illumination with a wavelength stimulating faster wound healing, such as for example, 450 nm or 550 nm.

As it was noted above a plurality of cartridges may be used with illumination module 1500 (FIG. 15). The optical radiation sources can be selected to provide visible, infrared (IR), blue, or even ultraviolet optical radiation at different intensity levels. For example, for acne treatment the user may test and select appropriate illumination cartridge matching the best for him or her acne treatment mode. The optical radiation sources may be operated in a continuous or pulse operation mode and according to fair or dark skin settings. Operation mode setting may be performed automatically by detecting the skin type by a skintype sensor, or set manually set, or preset according to the type of the cartridge.

The treatment may be enhanced by application to the same skin segment of radio frequency energy. The RF energy may be selected to heat the skin and tissue to an effective treatment temperature without ablating the skin. The combined energies of optical radiation in the appropriate spectrum range with radio frequency (RF) enable highly selective targeting of the sebaceous glands and acne bacteria. Infrared and RF energies reduce sebaceous gland activity while blue light simultaneously destroys active acne.

Figure 34:
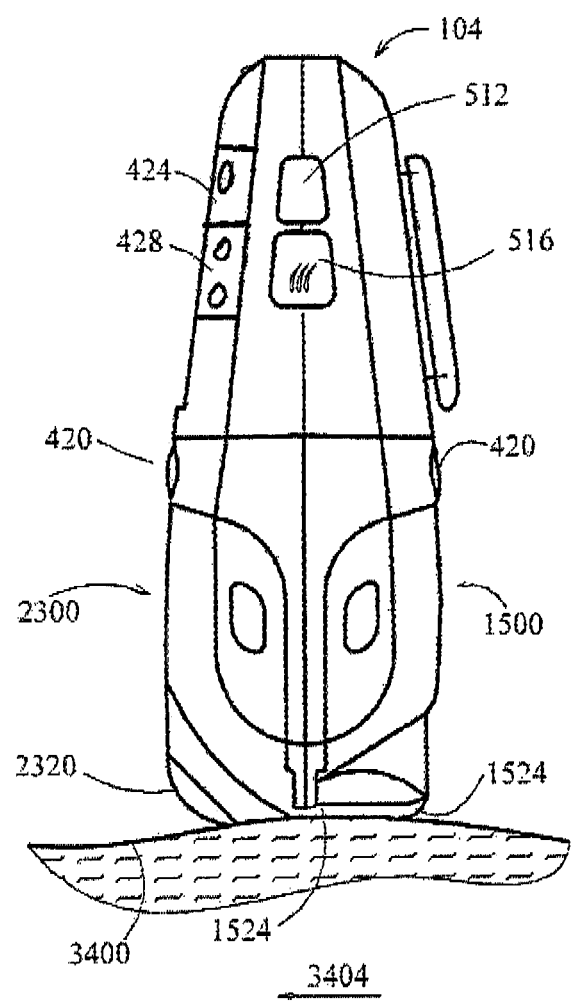
FIG. 34 is a schematic illustration of an additional exemplary method of skin treatment using the present applicator/device and apparatus.

FIG. 34 is a schematic illustration of an additional exemplary method of skin treatment using the present applicator and apparatus. Applicator 104 includes skin abrasion module 2300 (FIG. 23) and illumination module 1500 (FIG. 15). In this configuration applicator 104 may be used for such cosmetic skin treatment procedures as skin rejuvenation, wrinkle removal, acne treatment, skin pigmentation treatment, and other skin treatments. For skin treatment, applicator or device 104 is applied to a segment of skin 3400 to be treated and displaced by the user or as disclosed above by activating skin abrasion module 2300 and displaces applicator 104 in a desired direction indicated by arrow 3404, for example, along the segment of the skin to be treated. Operation of skin abrasion module 2300 removes the electrically isolating stratum corneum layer enabling easy access to bare epidermis layer. The particles of the exfoliated stratum corneum layer may be removed by vacuum. The skin exfoliation process increases blood and interstitial fluid flow to the treated skin segment and significantly reduces electrical resistance of the skin. Skin illumination module 1500 immediately follows abrasion module 2300. Low bare epidermis resistance enables firm or at least mostly firm contact between the RF electrodes 1524 and the skin 3400. Low electrical resistance of the treated skin enables application of relatively low frequency 300 kHz to 700 kHz deep into skin penetrating RF energy. The depth of RF energy penetration allows treating of collagen and adipose tissue containing layers. These frequencies are also effective in cellulite treatment and destruction. The treatment may be highly localized (corresponding to the distance between electrodes 1524 of illumination module 1500) and targeted for example, to double chin removal, small skin pigmentation spots removal, acne smoothing, and other treatments.

The process of skin exfoliation increases blood and interstitial fluid flow to the treated skin segment (stimulating circulation) further increasing heat absorption and accelerating appearance of the desired skin effect.

The skin abrasion treatment followed by RF and luminous energy application to bare epidermis layer removes dead cells, stimulates blood circulation enhancing heat in tissue conduction and dissipation, and rejuvenates the skin structure by replacing the old dull skin with fresh, younger cells and encouraging the regeneration of collagen and elastin for firmer, healthier looking skin.

Acne may be treated by a combination of abrasion module 2300 and illumination module 1500. Abrasion module removes a thin superficial skin layer and proper illumination wavelength of 500-550 nm may be used to speed-up the skin healing process.

In addition it is possible to supplement the treatment by applying topical agents such as a polyphenolic based antioxidant serum containing polyphenolic flavonoids and polyphenolic diterpenes (e.g., epigallocatechin, ursolic acid). This of course will improve even further the treatment results. See for example, Bruce M Freedman, "Topical antioxidant application augments the effects of intense pulsed light therapy" Journal of Cosmetic Dermatology, 8, 254-259, 2009.

Figure 35:
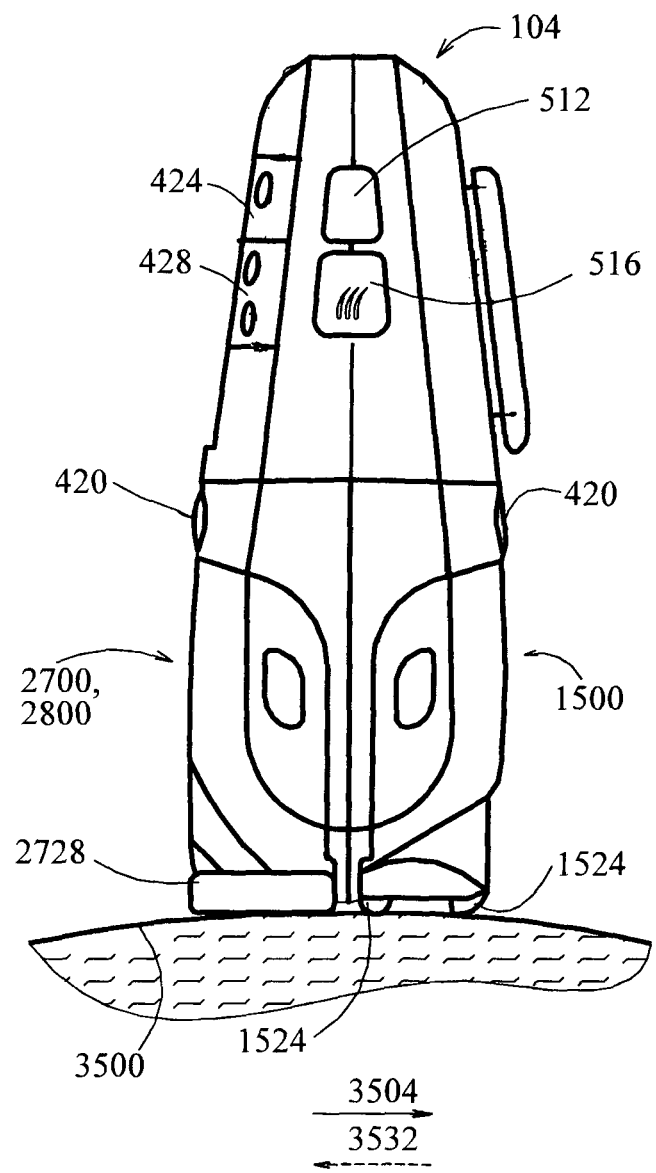
FIG. 35 is a schematic illustration of a further exemplary method of skin treatment using the present applicator/device and apparatus.

FIG. 35 is a schematic illustration of a further exemplary method of skin treatment using the present applicator/device and apparatus. Applicator 104 includes vacuum module 2700 (FIG. 27) or 2800 (FIG. 28) and illumination module 1500 (FIG. 15). In this configuration applicator 104 may be used for such cosmetic skin treatment procedures as acne treatment, waist tightening, skin pigmentation treatment, and other skin treatments. For skin treatment, the user applies applicator or device 104 to a segment of skin 3500 to be treated and activates skin illumination module 1500. The user displaces applicator 104 in a desired direction indicated by arrow 3504 or 3532, for example, along or across the segment of the skin to be treated. Operation of skin illumination module 1500 in pulse or continuous mode heats skin 3500, softens it and enables vacuum, applied by the vacuum module 2700 or 2800 following the illumination module 1500 to effectively pull out of the skin acne, whiteheads, blackheads, and other impurities. In addition to acne, the same process may be targeted for example, to small skin pigmentation spots removal, and other treatments. As noted above the suction enables better skin to illumination window and electrodes coupling and accordingly better treatment results.

Figure 36:
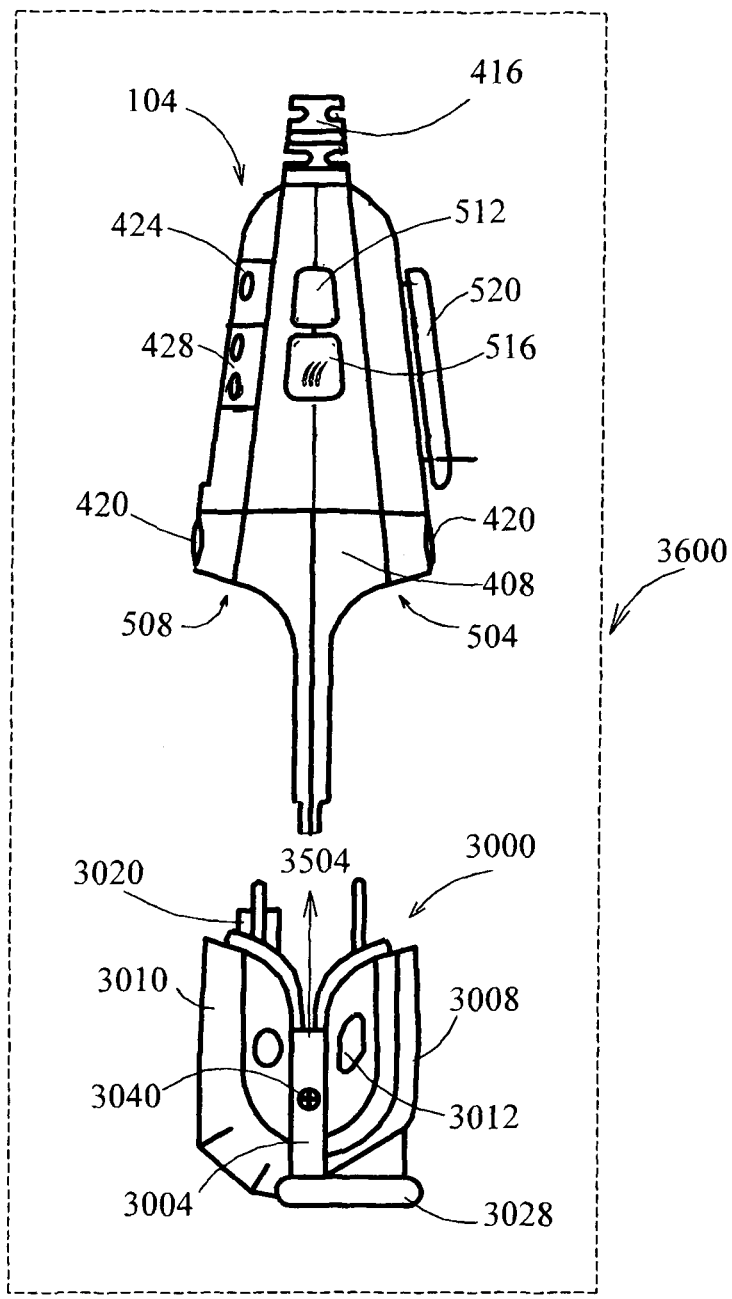
FIG. 36 is a schematic illustration of still another exemplary method of skin treatment using the present applicator/device and apparatus.

FIG. 36 is a schematic illustration of still another exemplary method of skin treatment using the present applicator/device and apparatus. Applicator 104 includes a combined illumination and RF module 1500 (FIG. 15) and a vacuum module 2800. In this configuration applicator 104 may be used for such cosmetic skin treatment procedures as acne treatment, skin pigmentation treatment, hair growth reduction, skin rejuvenation, skin tightening, and other skin treatments. For skin treatment, applicator or device 3600 is applied to a segment of skin to be treated and displaced by the user across the skin segment. RF energy is supplied to electrodes and it induces current in the skin. The current heats the skin and softens it. RF energy may be supplied in a continuous or pulse mode. Softened and heated skin enables vacuum, applied by the same module to effectively pull out of the skin acne, whiteheads, blackheads, and other impurities. Illumination module may include one or more light sources, for example LEDs, of different wavelength. Certain wavelengths may be applied to accelerate skin surface heating other wavelengths, for example blue or ultraviolet, may be applied to disinfect the treated skin segment accelerate skin healing and smoothing or skin rejuvenation.

The disclosed apparatus enables a casual user in a residential set-up to perform himself or herself almost every skin treatment procedure by using a variety of modules that may be inserted into the infrastructure frame. Although the applicator simultaneously receives only two types of skin treatment modules, these may be replaced after use for modules providing a different type of skin treatment. Such skin treatment modules like epilator, shaver, exfoliation or abrasive module and massage head apply a mechanical action to the skin. Ultrasound module applies ultrasound waves to the skin. Intense pulsed light and RF apply electromagnetic radiation to the skin. A combination of these modules may be used to provide a variety of skin treatments such as hair removal, skin rejuvenation, skin exfoliation, acne treatment, circumference reduction, and other skin treatments.

The effect of some of the treatments may be further enhanced by applying the treatment after a bath or shower when the skin is clean and soft. A combination of different modules providing different treatments to the same skin segment, for example heat and vacuum, mechanical hair removal and illumination and others help to combat almost all types of skin deficiencies regardless treated skin type.

Several embodiments have been described using detailed descriptions thereof that are provided by way of example and are not intended to be limiting. The described embodiments comprise different features, not all of which are required in all embodiments. Some embodiments utilize only some of the features or possible combinations of the features. Variations of embodiments that are described and embodiments comprising different combinations of features noted in the described embodiments will occur to persons of the art.

What is claimed is:

1. An apparatus for personal cosmetic skin treatment, said apparatus comprising:
   a hand-held applicator having an infrastructure frame, said frame including at least two receiving bays operatively configured to receive combinations of interchangeable cosmetic skin treatment modules occupying the at least two applicator bays simultaneously, each module in said combination operative to conduct a different cosmetic skin treatment process and operative to apply at least one of said cosmetic skin treatment processes alone or in combination simultaneously with its complement module, with each of the modules including at least an identification tag identifying the module and containing module operational parameters and at least one connector including a key mechanism that prevents insertion of a non-matching type of module into said applicator and wherein the modules are positioned relative to each other so that during directional movement of the applicator over the skin one module follows the other; and;

an applicator docking station including a control unit operative to provide to the applicator power supply, fluids required for applicator operation, and control the applicator movement; and wherein the control unit communicates with the identification tag, identifies the received module, and automatically sets the skin treatment parameters.

2. The apparatus according to claim 1, wherein the applicator infrastructure frame including one or more receiving bays receives at least one of a group of interchangeable modules operative to perform a cosmetic skin treatment, said group consisting of modules for mechanical hair removal, modules for wrinkle removal, modules for skin rejuvenation, modules for acne treatment, modules for collagen tightening, modules for skin illumination, a module for skin abrasion; and wherein each of the interchangeable modules have identical mechanical and electrical interfaces and each of the modules has at least one identification tag.

3. The apparatus according to claim 1 wherein the applicator further comprises at least one sensor selected from a group of sensors consisting of direction sensors, micro switches, temperature sensors, and impedance sensors; and wherein the direction sensor is operative to activate at least one of the modules according to the applicator displacement direction when the applicator is applied to a subject skin and displaced over the skin and the micro switches are operative to activate at least one of the modules when the applicator is gripped by a subject.

4. The apparatus according to claim 3, wherein the temperature sensor is operative to change the operation mode of at least one of the modules according to the temperature readings or the rate of temperature change.

5. The apparatus according to claim 1 wherein the module identification tag is one of a group consisting of an RFID device or an EEPROM.

6. The module according to claim 1, wherein the tag identifying the module comprises a permanent data record which stores the type of the module, type of recommended treatment and recommended treatment parameters, and a variable data record enabling to record the amount of events in course of which the module was operative; and wherein the data recorded into the tag enables upon the tag insertion into the applicator operation of the module.

7. The apparatus according to claim 1, wherein said module combinations include an illumination module and vacuum module, an illumination module and an epilator module, a skin rejuvenation module and a skin illumination module and an illumination and RF module and a vacuum module.

8. The apparatus according to claim 1, also including a grip sensor that when pressed by a user, enables different voltage supplies to different functional modules inserted into said receiving bays of said applicator.

9. The apparatus according to claim 2, wherein the skin illumination module is a disposable cartridge including:

at least one of a group of illumination sources consisting of an incandescent lamp, xenon lamp, Xenon IPL lamp, laser diode, LED, laser or a combination of two or more of these sources;

a reflector with opening and elements operative to direct a cooling flow to cool the source of optical radiation, said reflector configured to reflect illumination generated by the illumination sources to the treated segment of the skin; and at least one dielectric coated protective window coupled with the reflector and configured to form a cooling flow pass between the dielectric coated protective window and the reflector.

10. The apparatus according to claim 2, wherein the skin illumination module also includes a pair of side mirrors operative to collect and direct stray illumination to the treated segment of the skin.

11. The apparatus according to claim 1, wherein the applicator comprises a case incorporating at least a control unit being in communication with the identification tag of each of the modules and according to skin type treated automatically setting at least one of a group of treatment parameters consisting of the RF power, IPL pulse repetition rate, and IPL power.

* * * * *